US009480519B2

(12) United States Patent
Suddaby

(10) Patent No.: US 9,480,519 B2
(45) Date of Patent: Nov. 1, 2016

(54) APPARATUS FOR ALIGNING A SPINE USING DEPLOYABLE BONE ANCHORS AND METHOD FOR THE SAME

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 0 days.

(21) Appl. No.: 14/244,241

(22) Filed: Apr. 3, 2014

(65) Prior Publication Data

US 2015/0196342 A1 Jul. 16, 2015

Related U.S. Application Data

(63) Continuation-in-part of application No. 13/644,365, filed on Oct. 4, 2012, now Pat. No. 8,764,803.

(51) Int. Cl.
| | | |
|---|---|---|
| *A61B 17/70* | (2006.01) | |
| *A61B 17/88* | (2006.01) | |
| *A61B 17/86* | (2006.01) | |
| *A61B 17/17* | (2006.01) | |
| *A61B 17/66* | (2006.01) | |
| *A61B 17/68* | (2006.01) | |
| *A61B 17/00* | (2006.01) | |
| *A61B 17/56* | (2006.01) | |

(52) U.S. Cl.
CPC ....... *A61B 17/8869* (2013.01); *A61B 17/1757* (2013.01); *A61B 17/66* (2013.01); *A61B 17/683* (2013.01); *A61B 17/7053* (2013.01); *A61B 17/7059* (2013.01); *A61B 17/8685* (2013.01); *A61B 17/8855* (2013.01); *A61B 17/885* (2013.01); *A61B 17/8852* (2013.01); *A61B 17/8858* (2013.01); *A61B 2017/00004* (2013.01); *A61B 2017/565* (2013.01); *A61B 2017/681* (2013.01)

(58) Field of Classification Search
CPC A61B 17/66; A61B 17/885; A61B 17/8852; A61B 17/8855; A61B 17/8858; A61B 2017/681; A61B 17/0004
See application file for complete search history.

(56) References Cited

U.S. PATENT DOCUMENTS

| | | | |
|---|---|---|---|
| 1,949,969 | A | 3/1934 | Longfellow |
| 2,867,819 | A | 1/1959 | George |
| 3,809,074 | A | 5/1974 | De Moude |
| 4,047,523 | A | 9/1977 | Hall |
| 4,273,116 | A | 6/1981 | Chiquet |
| 5,122,140 | A | 6/1992 | Asche et al. |
| 5,782,831 | A | 7/1998 | Sherman et al. |

(Continued)

OTHER PUBLICATIONS

Cundy, Peter J.; Paterson, Dennis C.; Hillier, Terence M.; Sutherland, Andrew D.; Stephen, John P.; Foster, Bruce K., Cotrel-Dubousset Instrumentation and Vertebral Rotation in Adolescent Idiopathic Scoliosis. The Journal of Bone and Joint Surgery, 1990, pp. 670-674, J Bone Joint Surg, British Editorial Society of Bone and Joint Surgery.

*Primary Examiner* — Ellen C Hammond
(74) *Attorney, Agent, or Firm* — Simpson & Simpson, PLLC

(57) ABSTRACT

An assembly for performing a gradual lateral spinal alignment of a spine. The assembly includes an inflatable bone anchor that includes an inflatable balloon, a hollow tube attached to the balloon and attached to an external support, such as a brace. The inflatable balloon extends into or through a vertebra of the misaligned spine and deployed. The inflatable balloon is pulled using the vertebra and attached to the brace to pull the spine into alignment. The device allows the spine to be gradually placed into alignment helping to avoid trauma on the spine and surrounding tissue.

10 Claims, 21 Drawing Sheets

(56) References Cited

U.S. PATENT DOCUMENTS

| | | | |
|---|---|---|---|
| 5,863,292 A | 1/1999 | Tosic | |
| 5,893,850 A | 4/1999 | Cachia | |
| 5,928,230 A | 7/1999 | Tosic | |
| 6,033,429 A | 3/2000 | Magovern | |
| 6,077,268 A | 6/2000 | Farris et al. | |
| 6,086,590 A | 7/2000 | Margulies et al. | |
| 6,146,386 A | 11/2000 | Blackman et al. | |
| 6,290,700 B1 | 9/2001 | Schmotzer | |
| 6,423,065 B2 | 7/2002 | Ferree | |
| 6,551,320 B2 | 4/2003 | Lieberman | |
| 6,648,890 B2 | 11/2003 | Culbert et al. | |
| 6,676,665 B2 | 1/2004 | Foley et al. | |
| 7,632,277 B2 | 12/2009 | Woll et al. | |
| 7,842,072 B2 | 11/2010 | Dawson | |
| 8,083,741 B2 | 12/2011 | Morgan et al. | |
| 8,162,979 B2 | 4/2012 | Sachs et al. | |
| 8,267,971 B2 * | 9/2012 | Dutoit | A61B 17/68 606/246 |
| 8,323,294 B2 | 12/2012 | Mickiewicz et al. | |
| 8,512,343 B2 | 8/2013 | Dziedzic et al. | |
| 8,672,944 B2 | 3/2014 | Boachie-Adjei et al. | |
| 2003/0120301 A1 * | 6/2003 | Yock | A61B 18/245 606/194 |
| 2004/0049202 A1 | 3/2004 | Berger | |
| 2004/0097944 A1 | 5/2004 | Koman et al. | |
| 2006/0047282 A1 | 3/2006 | Gordon | |
| 2006/0195090 A1 | 8/2006 | Suddaby | |
| 2006/0217736 A1 * | 9/2006 | Kaneko | A61B 17/7097 606/94 |
| 2007/0270876 A1 * | 11/2007 | Kuo | A61B 17/1617 606/92 |
| 2008/0051707 A1 | 2/2008 | Phan et al. | |
| 2009/0088799 A1 | 4/2009 | Yeh | |
| 2009/0093820 A1 | 4/2009 | Trieu et al. | |
| 2009/0112262 A1 | 4/2009 | Pool et al. | |
| 2009/0112263 A1 | 4/2009 | Pool et al. | |
| 2009/0281575 A1 | 11/2009 | Carls et al. | |
| 2011/0066188 A1 | 3/2011 | Seme et al. | |
| 2011/0230806 A1 | 9/2011 | Lou et al. | |
| 2011/0295170 A1 | 12/2011 | Laranjeira Gomes et al. | |
| 2012/0016369 A1 * | 1/2012 | O'Halloran | A61B 17/7097 606/93 |
| 2012/0016371 A1 | 1/2012 | O'Halloran et al. | |
| 2012/0157996 A1 | 6/2012 | Walker et al. | |

\* cited by examiner

APPARATUS FOR ALIGNING A SPINE USING DEPLOYABLE BONE ANCHORS AND METHOD FOR THE SAME

This application is filed under 35 U.S.C. §120 as a continuation-in-part patent application of U.S. patent application Ser. No. 13/644,365, filed Oct. 4, 2012, which application is incorporated herein by reference in its entirety.

The present invention relates to the field of surgical devices, particularly to orthopedic surgical devices, and more particularly to corrective devices related to the spine.

BACKGROUND OF THE INVENTION

Scoliosis is a disorder that causes an abnormal curvature of the spine, or backbone. Patients with scoliosis develop abnormal curves to either side of the body's median line (lateral curve) and the bones of the spine twist on each other like a corkscrew. Scoliosis is about two times more common in girls than boys. It can be seen at any age, but it is most common in those over 10 years old.

Often, the cause of scoliosis is unknown and is described based on the age when scoliosis develops. If the person is less than 3 years old, it is called infantile idiopathic scoliosis. Scoliosis that develops between 3 and 10 years of age is called juvenile idiopathic scoliosis, and people that are over 10 years old have adolescent idiopathic scoliosis.

In functional scoliosis, the spine is normal, but an abnormal curve develops because of a problem somewhere else in the body. This could be caused by one leg being shorter than the other or by muscle spasms in the back. In the neuromuscular form, there is a problem during the formation of the bones of the spine. Either the bones of the spine fail to form completely or they fail to separate from each other. This type of scoliosis may develop in people with other disorders including birth defects, muscular dystrophy, cerebral palsy, and Marfan's disease. This type of scoliosis is often much more severe and needs more aggressive treatment than other forms of scoliosis. Degenerative scoliosis occurs in older adults. It is caused by changes in the spine due to arthritis. Weakening of the normal ligaments and other soft tissues of the spine combined with abnormal bone spurs can lead to an abnormal curvature of the spine.

Adolescent idiopathic scoliosis is the most common form of scoliosis. If the angle of the spinal curve (Cobb's angle) is small when first diagnosed, it can be observed and followed with routine X-rays and measurements. If the curve stays below 25 degrees, no other treatment is usually needed. If the curve is between 25-40 degrees, a brace may be recommended. If the curve is greater than 40 degrees, then surgery may be recommended. Braces are not designed to correct the curve. They are used to help slow or stop the curve from getting worse.

Spinal fusion is one surgical procedure that may be used to alleviate scoliosis. In this procedure, bone is grafted to the vertebrae to form a rigid column. The rigidity of the column will prevent the curve from worsening. However, the rigid column reduces the range of motion available to the patient.

Modern surgical procedures attempt to address sagittal imbalance and rotational defects unresolved by the earlier rod systems. They primarily involve a combination of rods, screws, hooks, cables and/or wires fixing the spine and applying forces to the spine to correct the spinal curvature. An example of the use of screws and cables is seen in U.S. Patent Application Publication No. 2006/0195090 to Suddaby ("Suddaby") which is hereby incorporated by reference in its entirety. Suddaby discloses a system for improving the alignment of a spine by placing a series of screws or pins into the posterior or lateral side of the bodies of individual vertebrae. Hollow spacers are placed between the pins and a cable is extended through the heads of the pins and the spacers and is attached to an expansion sleeve. Tension is applied to the cable by pulling it through the expansion sleeve and then applying tension to the cable to pull the attached pins into an improved alignment. One of a plurality of nodules at the end of the cable is then placed into the passage of the expansion sleeve thereby holding the cable in the new "tensioned" position. The tension discourages movement of the spine.

U.S. Pat. No. 6,551,320 to Lieberman ("Lieberman"), hereby incorporated by reference in its entirety, discloses an apparatus for aligning a spine that includes a plurality of anchors screwed into adjacent vertebral bodies. A cable or series of cables is strung through or around the anchors and then pulled. The tension applied to the cable(s) is used to pull the spine into a desired alignment. U.S. Patent Application Publication No. 2009/0112262 to Pool, et al. ("Pool"), hereby incorporated by reference in its entirety, discloses a system in which at least one anchor is screwed or otherwise embedded into an upper vertebra and one or more anchors are similarly placed in lower vertebra(ae). A cable is extended between the anchors and force applied to the cable by a magnetic adjustment device to align the spine. In some cases a second anchor-cable arrangement can be used on the opposite side of the spine.

Finally, U.S. Pat. No. 5,782,831 to Sherman, et al. ("Sherman"), hereby incorporated by reference in its entirety, discloses a system for reducing a displaced vertebra between adjacent vertebrae. The Sherman patent describes a system in which two anchors are screwed into the vertebrae on either side of the displaced vertebra with a rod attached between the anchors. A third anchor is screwed into the displaced vertebra and attached to a cable. A cable tightening device, such as a come-along type device is used to pull the displaced vertebra into alignment after which it is attached to the support rod. However, the attachment of a bar across three adjacent vertebrae prevents pulling a curved spine into a more proper alignment.

In attempting to solve spinal alignment and displacement problems, the prior art relies on multiple vertebral anchors and the application of alignment force through complicated force applicators and cable systems. Often such corrective systems fail to provide complete correction of spinal alignment as full recuperation requires either too much force to correct the curve or sudden, rapid stretching of spinal neural elements resulting in permanent neurological damage. Because direct visualization of the individual spinal elements is often required for the above techniques, lengthy incisions and large spinal dissections are required to expose the spinal segments requiring treatment. Even with these major life threatening surgeries, perfect spinal alignment is rarely, if ever, achieved.

FIGS. 2A and 2B depict typical braces used by patients afflicted with scoliosis. FIG. 2A shows a rear view of typical full body brace 4 used to prevent further deterioration of spinal alignment. FIG. 2B shows a rear view of typical brace 5 used to prevent further deterioration of spinal alignment. In some cases, braces such as braces 4 and 5 may improve the condition, but they rarely enable the wearer to achieve a full recovery to a correct spinal alignment.

What is needed then is an apparatus for aligning the spine that possesses few parts and is easy to implant while enabling a gradual restoration of the spinal alignment over a determined period of time so that large and/or sudden forces are not applied to the curved spine. By applying reduced corrective forces over a longer period of time, complications such as bone fracture and nerve damage can be reduced or avoided. Moreover, it would be advantageous in the art of neurosurgery and orthopedic surgery to align a spine with simple percutaneous methods so that endoscopic or minimally invasive techniques can be employed.

SUMMARY OF THE INVENTION

The present invention broadly comprises an assembly for performing a gradual lateral spinal alignment of a spine, the spine to be realigned having a lateral curve, the lateral curve having a convex side and an opposite concave side. The assembly comprises a hollow bone screw having internal threads and an open proximal end and an open distal end, a second screw threadably inserted into the hollow bone screw, a toggle bolt that includes a shaft having a distal end and a proximal end, wherein the distal end supports a pivotal attachment, and a toggle wing pivotably attached to the pivotal attachment. The assembly also includes a rigid stabilizing rod, the stabilizing rod having two ends and defining a first orifice and a second orifice, such that the axis of the second orifice is perpendicular to the axis of the first orifice and the second orifice is surrounded by an externally threaded annular lip, a cable having a first end and a second end, the first end attached to the proximal end of the toggle bolt and extending through second orifice, and a tube enclosing at least part of the length of the cable and having a first end threadably attached to the externally threaded annular lip, such that one end of the toggle bolt is extended through the distal end of the hollow screw.

The invention also broadly comprises a method of gradually laterally aligning a spine having a lateral curve using a spinal alignment assembly the spinal alignment assembly including a hollow bone screw having internal threads and an open proximal end and an open distal end, a second screw threadably inserted into the hollow bone screw; a toggle bolt that includes a shaft having a distal end, a middle section, and a proximal end, wherein the distal end supports a pivotal attachment, and a toggle wing pivotably attached to the pivotal attachment. The assembly also includes a rigid stabilizing rod, the stabilizing rod having two ends and defining a first orifice and a second orifice, wherein the axis of the second orifice is perpendicular to the axis of the first orifice and the second orifice is surrounded by an externally threaded annular lip, a cable having a first end and a second end, the first end attached to the proximal end of the toggle bolt and extending the second orifice, and a tube enclosing at least part of the length of the cable and having a first end threadably attached to the externally threaded annular lip and a second set screw threadably inserted into the tube, such that one end of the toggle bolt is extended through the distal end of the hollow screw. The gradual alignment method comprises the steps of screwing the hollow bone screw into a body of a vertebra of the spine; removing the second inner screw from the hollow bone screw; extending the toggle bolt through the hollow bone screw; placing the stabilizing rod on the hollow bone screw between the spine and the receiver; deploying the toggle wing on a convex side of the lateral curve; aligning the stabilizing rod laterally and longitudinally along the concave side of the lateral curve of the spine; enclosing at least part of the length of the cable in the tube such that the second end of the cable extends out of the back of a user; threadably attaching the tube to the receiver; attaching a cable tightening device at or near the second end of the cable; pulling the cable so as to pull the toggle bolt and the vertebra toward the concave side of the lateral curve; and tightening the second set screw to the cable to hold the pulled toggle bolt in the pulled position.

The present invention also broadly comprises an assembly for performing a gradual spinal alignment comprising: a first external leverage support and an inflatable bone anchor attached to the external leverage support, the inflatable bone anchor including a proximal tube having proximal and distal ends and attached to the external leverage support and at least one distal inflatable balloon anchor at the distal end. The tube is attached to the external leverage support at the proximal end. In a preferred embodiment, the present invention also includes a pulling device such as, but not limited to, a pliers, a winch, or a come-along. In an alternate embodiment, the invention further includes a second external leverage support; at least one strut extending from the second external leverage support; and, a bone screw extending from each of the at least one strut.

The present invention also broadly comprises a method of gradually aligning a spine having a lateral curve using a spinal alignment assembly, the lateral curve having a concave side and a convex side, the spinal alignment assembly comprising: a first external leverage support; an inflatable bone anchor attached to the external leverage support, the inflatable bone anchor including a tube attached to at least one distal inflatable balloon anchor, a pulling device attached to the proximal end of the tube of the inflatable bone anchor; wherein the proximal tube is attached to the external leverage support; wherein the first external leverage support is a body brace; the method comprising: drilling a hole into a vertebral body on the concave side; inserting the at least one distal inflatable balloon into the hole; inflating the at least one distal balloon to form a cavity within the vertebra body; pulling the bone anchor at the proximal end to pull the lateral curve toward the concave side; and attaching a proximal end of the inflatable bone anchor to the brace.

A first object of the invention is to provide a device for aligning a lateral curve in a spine using simple percutaneous methods and minimally invasive techniques, such as endoscopic techniques.

A second object of the invention is to provide a method in which the alignment device may be resorbed into the body.

A third object of the invention is to supply a device and method of spinal alignment in which corrective alignment is achieved gradually to avoid potential neurological and muscular damage. The term "gradually" means over a period of several weeks to several months depending on the severity of the lateral curve.

An additional object of the invention is to offer a device and method using a firm support device such as a body brace for leverage support.

A further object of the invention is to present a spinal alignment method in which both sides of the spinal column may be subject to an alignment procedure at the same time.

A still further object of the invention is to provide a device for aligning a lateral curve in a spine using a minimum amount of vertebral drilling sites.

BRIEF DESCRIPTION OF THE SEVERAL VIEWS OF THE DRAWINGS

The nature and mode of the operation of the present invention will now be more fully described in the following detailed description of the invention taken with the accompanying drawing Figures, in which.

DETAILED DESCRIPTION OF EMBODIMENTS OF THE INVENTION

At the outset, it should be appreciated that like drawing numbers on different drawing views identify identical structural elements of the invention. It also should be appreciated that figure proportions and angles are not always to scale in order to clearly portray the attributes of the present invention.

While the present invention is described with respect to what is presently considered to be the preferred embodiments, it is understood that the invention is not limited to the disclosed embodiments. The present invention is intended to cover various modifications and equivalent arrangements included within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
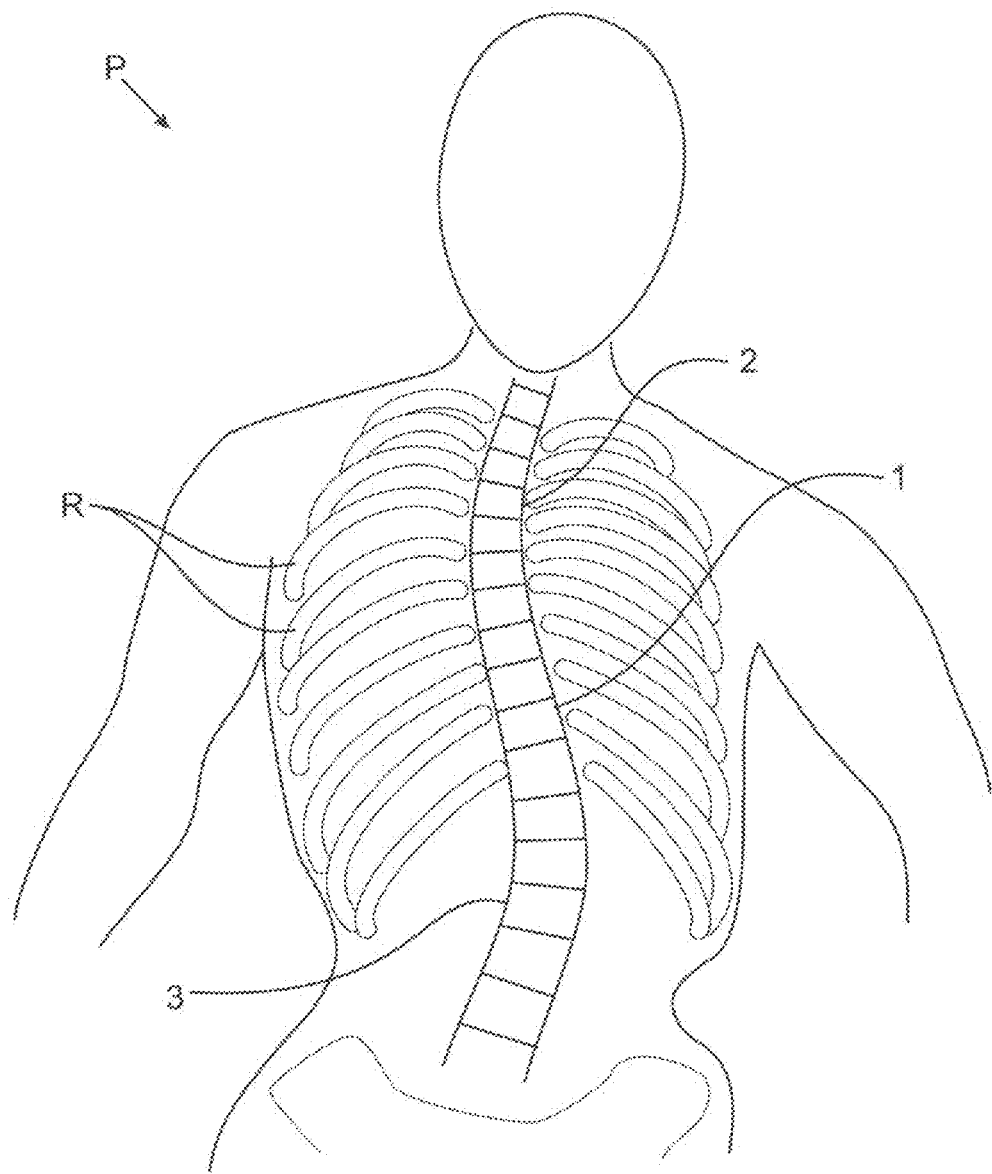
FIG. 1 is a stylized drawing of person with a spine afflicted with scoliosis.
Figure 2A:
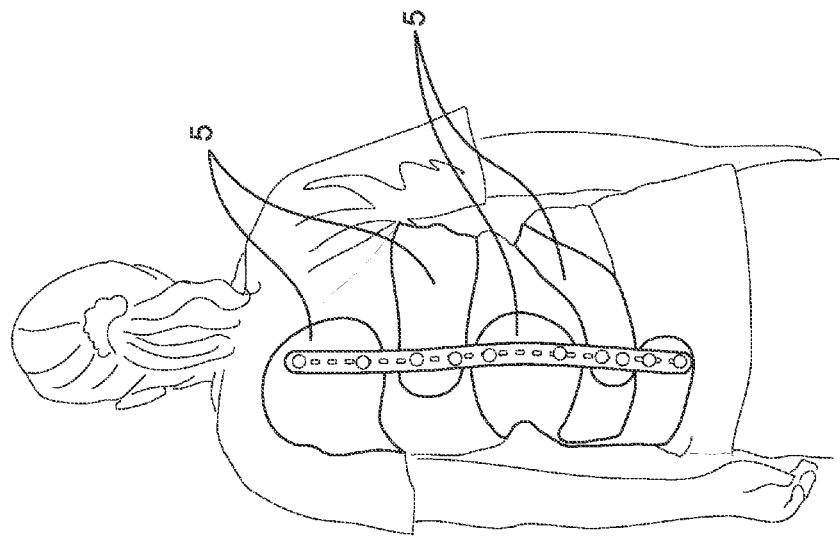
FIG. 2A is a rear view of a typical full body brace used by scoliosis patients.
Figure 2B:
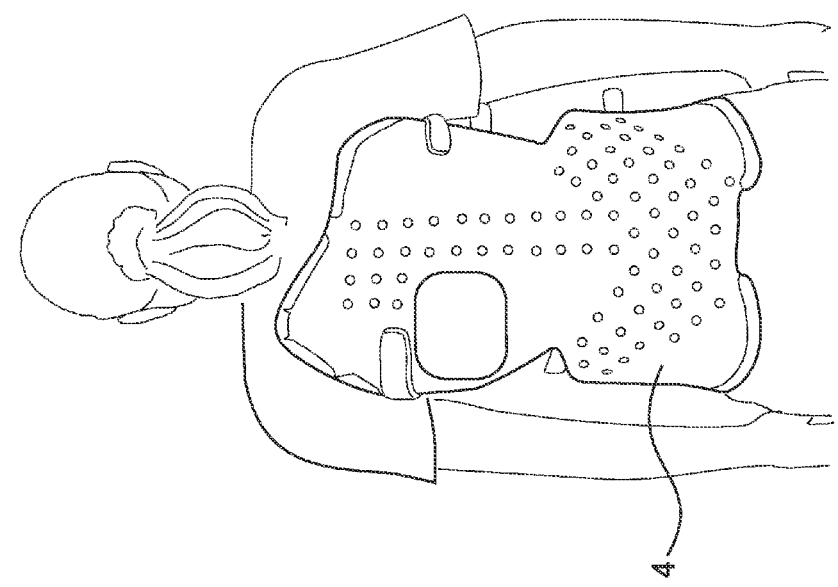
FIG. 2B is a rear view of a lighter typical brace used by scoliosis patients.

Adverting to the drawings, FIG. 1 is a stylized view of person P with a spine afflicted with scoliosis. Spinal column 1 is shown to have two lateral curves—upper curve 2 and lower curve 3. Often the presence of one lateral curve will generate the formation of a second curve to compensate for the reduced spinal support of the body caused by one lateral curve.

Figure 3:
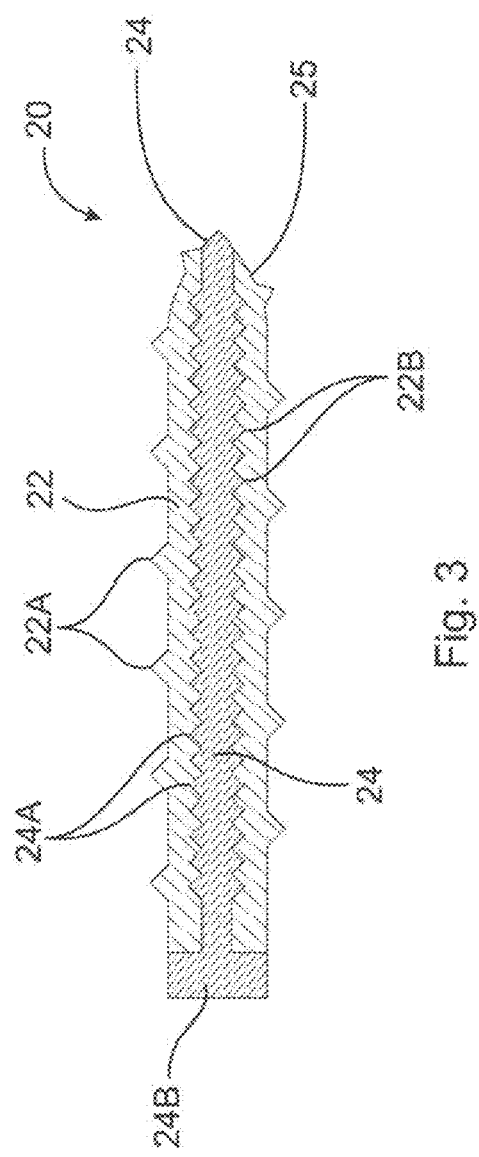
FIG. 3 is a cross sectional view of a hollow bone screw having an outer shell and an inner screw threadably inserted therein.
Figure 4A:
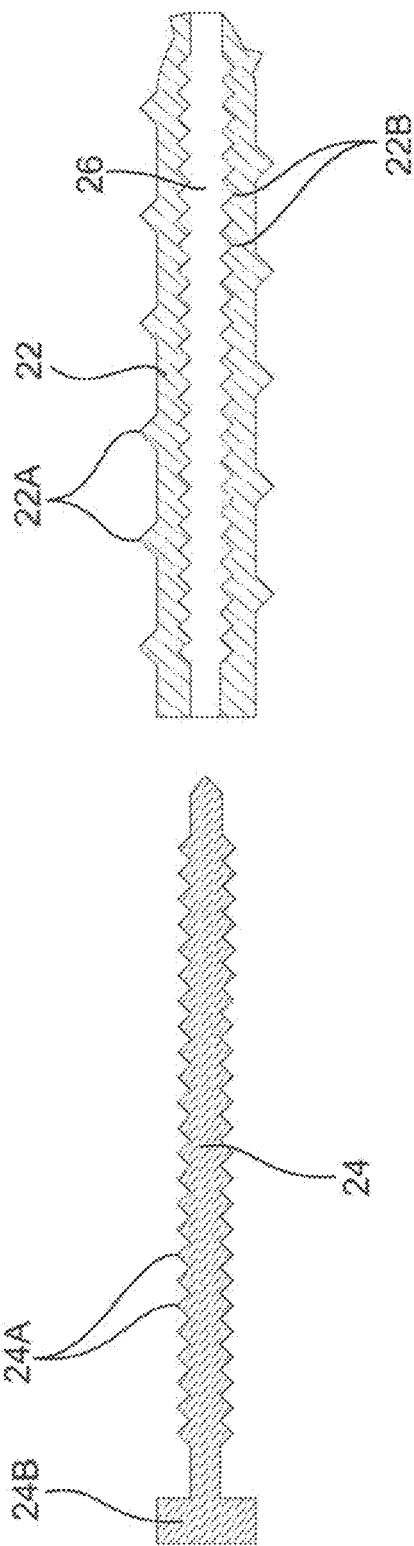
FIG. 4A shows a cross sectional view of the outer shell shown in FIG. 3 isolated from the inner screw.
Figure 4:
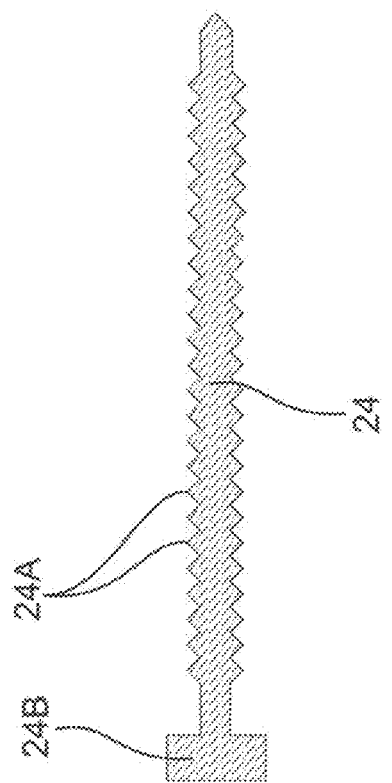
FIG. 4 shows a cross sectional view of the inner screw shown in FIG. 3 isolated from the outer shell.

FIG. 3 is a cross sectional view of hollow bone screw 20. Hollow bone screw 20 includes outer screw shell 22 and inner screw 24. Outer screw shell 22 is externally threaded with threads 22a to enable it to be screwed into the body of a vertebra as described below. Inner screw 24 is also externally threaded with threads 24a to threadably connect with internal threads 22b of outer screw shell 22. Preferably cap 24b is attached to the proximal end of inner screw 24. FIG. 4A shows inner screw 24 isolated from outer screw shell 22 shown in FIG. 3. FIG. 4B shows outer screw shell 22 isolated from inner screw 24 shown in FIG. 3. When inner screw 24 is removed from outer screw shell 22, lumen 26 remains as a hollow space along the length of outer screw shell 22.

Figure 5:
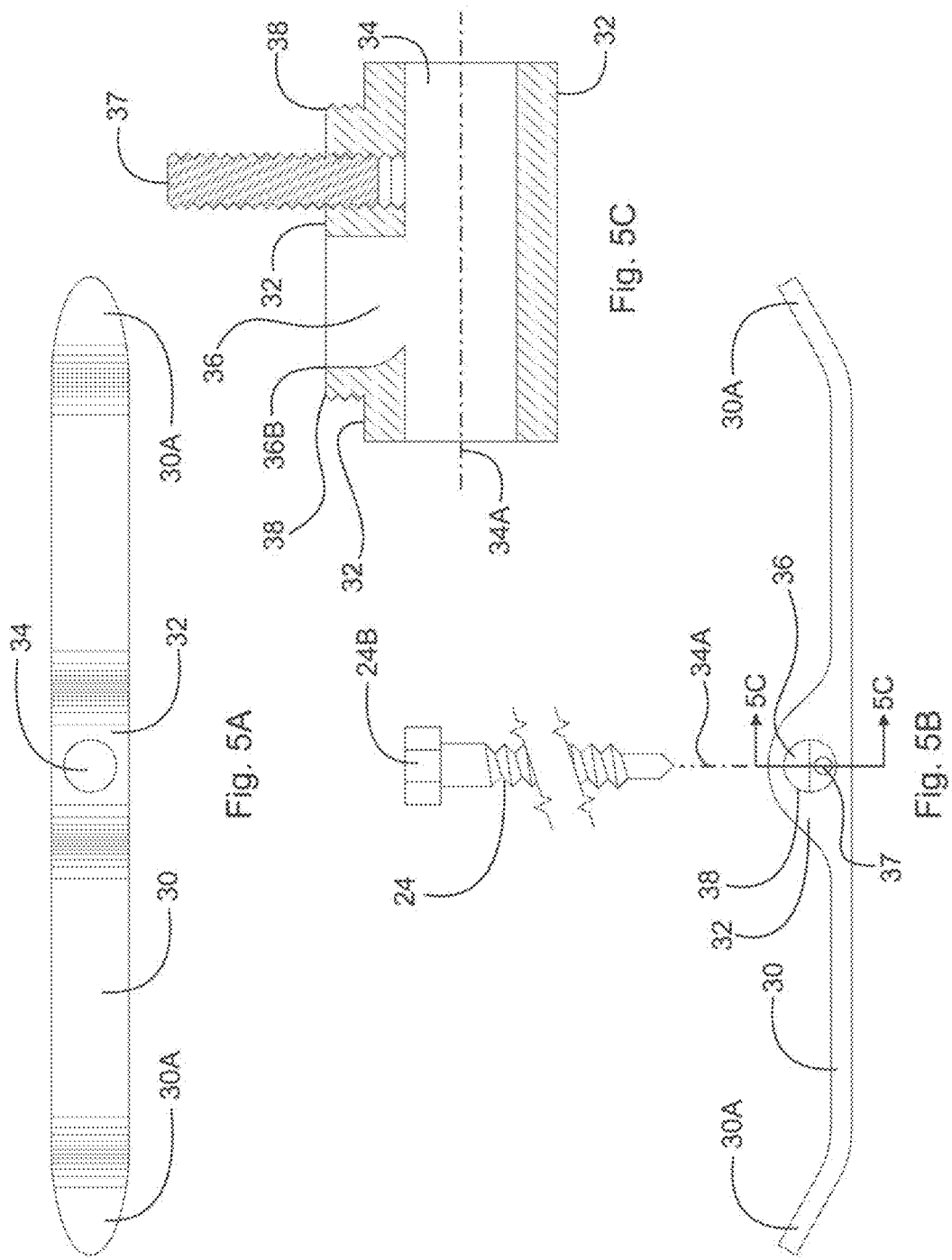
FIG. 5A is a top view of the stabilizing rod of the assembly of the present invention.
FIG. 5B is a side view of the stabilizing rod shown in FIG. 5A including the receiver formed into the peak that defines a screw hole.
FIG. 5C is a cross sectional view taken generally along line 5C-5C in FIG. 5B.

FIG. 5A is a top view of stabilizing rod 30 ("rod 30"). FIG. 5B is a side view of rod 30 showing receiver 32 formed into a peak that defines screw hole 34 (not seen in FIG. 5B). FIG. 5C is a cross sectional view taken generally along line 5C-5C in FIG. 5B. Preferably ends 30a of rod 30 are curved to provide the advantage of being able to move more easily along the spine and longitudinal muscles along the spine. Receiver complex 32 ("receiver 32") extends from the surface of rod 30 to form a peak which defines screw hole 34. Also seen is aperture 36, defined by part of one side of receiver 32, and set screw 37 set into the same side of receiver 32.

Set screw 37 is shown set into receiver 32. It can be seen that aperture 36 and set screw 37 have parallel longitudinal-axes and both of these axes are substantially perpendicular to axis 34a of screw hole 34. Annular lip 38 surrounds aperture 36 and set screw 37 and is externally threaded.

Figure 6:
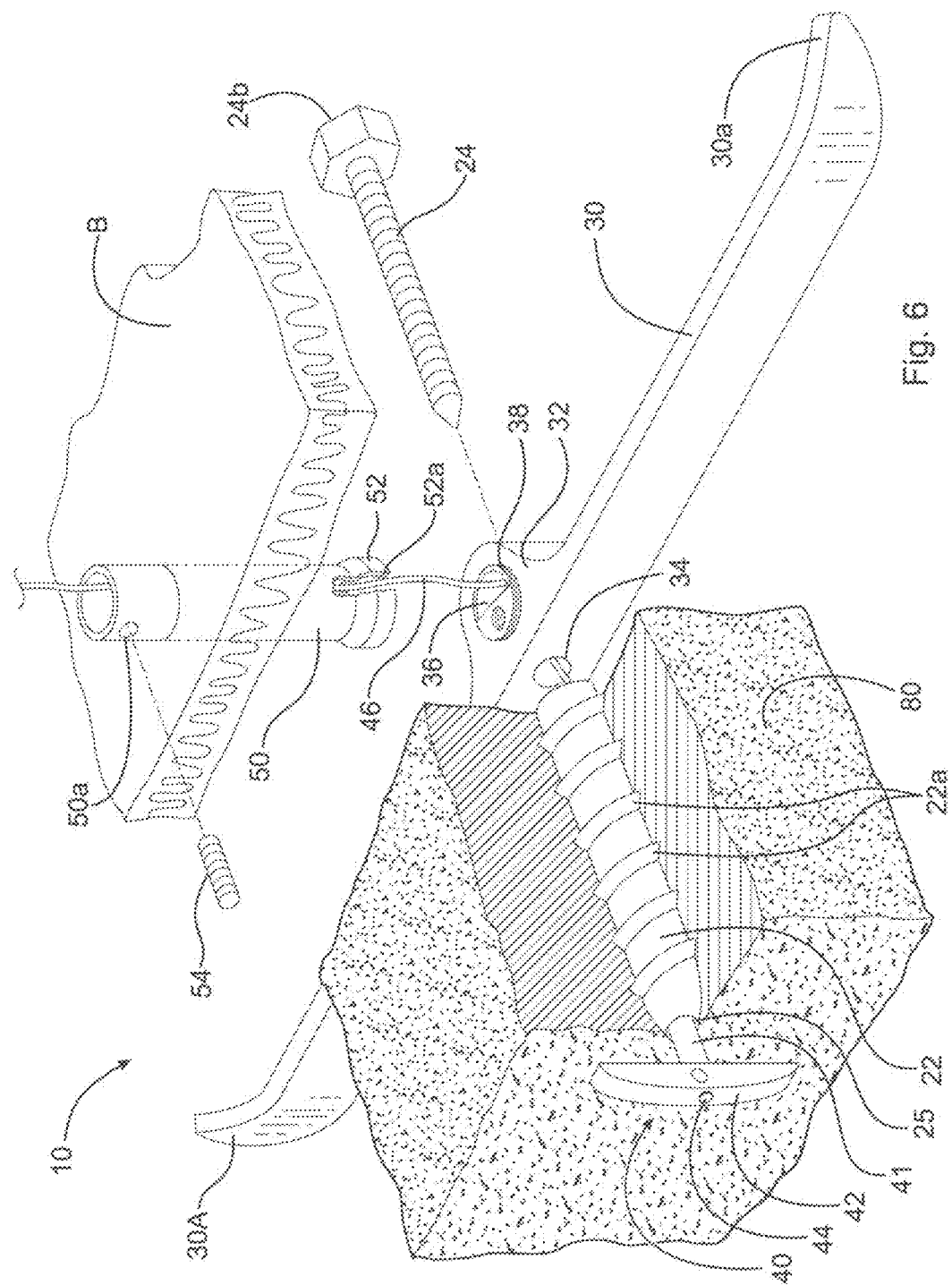
FIG. 6 is side perspective partial exploded and fragmentary view of the assembly of the present invention attached to a vertebra in the spinal column of the spine to be aligned.

FIG. 6 is side perspective partial exploded view of assembly 10 attached to vertebra 80 in a spinal column of a spine to be aligned. Initially, hollow screw 20 is extended into screw hole 34 and is screwed into body 80 of the target vertebra until distal end point 25 emerges slightly from the distal side, which preferably is at or near the peak of the convex curve of laterally curved spinal column 1. Inner screw 24 is then removed from outer shell 22 thereby opening lumen 26. Toggle bolt 40 having shaft 41 with a distal end and a proximal end (not seen in FIG. 6) and deployable wings 42 is guided through lumen 26 from the proximal side of vertebra 80 until it extends past distal end point 25 at the distal end of hollow screw 20. Preferably, toggle bolt 40 includes pivot attachment 44 to which wings 42 are attached. Wings 42 are deployed (opened out) as shown in FIG. 6 and pulled against the convex side of vertebra 80. Cable 46, attached to the proximal end of shaft 41, extends out the proximal end of lumen 26 and guided into screw hole 34 and up aperture 36. This perpendicular turn is preferably guided by curved wall 36b of aperture 36. Persons of skill in the art will recognize that cable 46 may be threaded from distal end point 25 toward the proximal end of lumen 26 with wings 46 deployed at distal end point 25. In addition, equivalent devices having expanded or expandable components positioned similarly to wings 46 may be used in place of toggle bolt 40 as long as they provide satisfactory support for pulling cable 46 as described below.

Cable 46 is guided through tube 50 which extends posteriorly through back B. Lip 52 at one end of tube 50 includes internal threads 52a to enable tube 50 to be threadably attached to annular lip 38. Set screw 54 is screwed into threaded tube aperture 50a to hold cable 46 in place.

Figure 7:
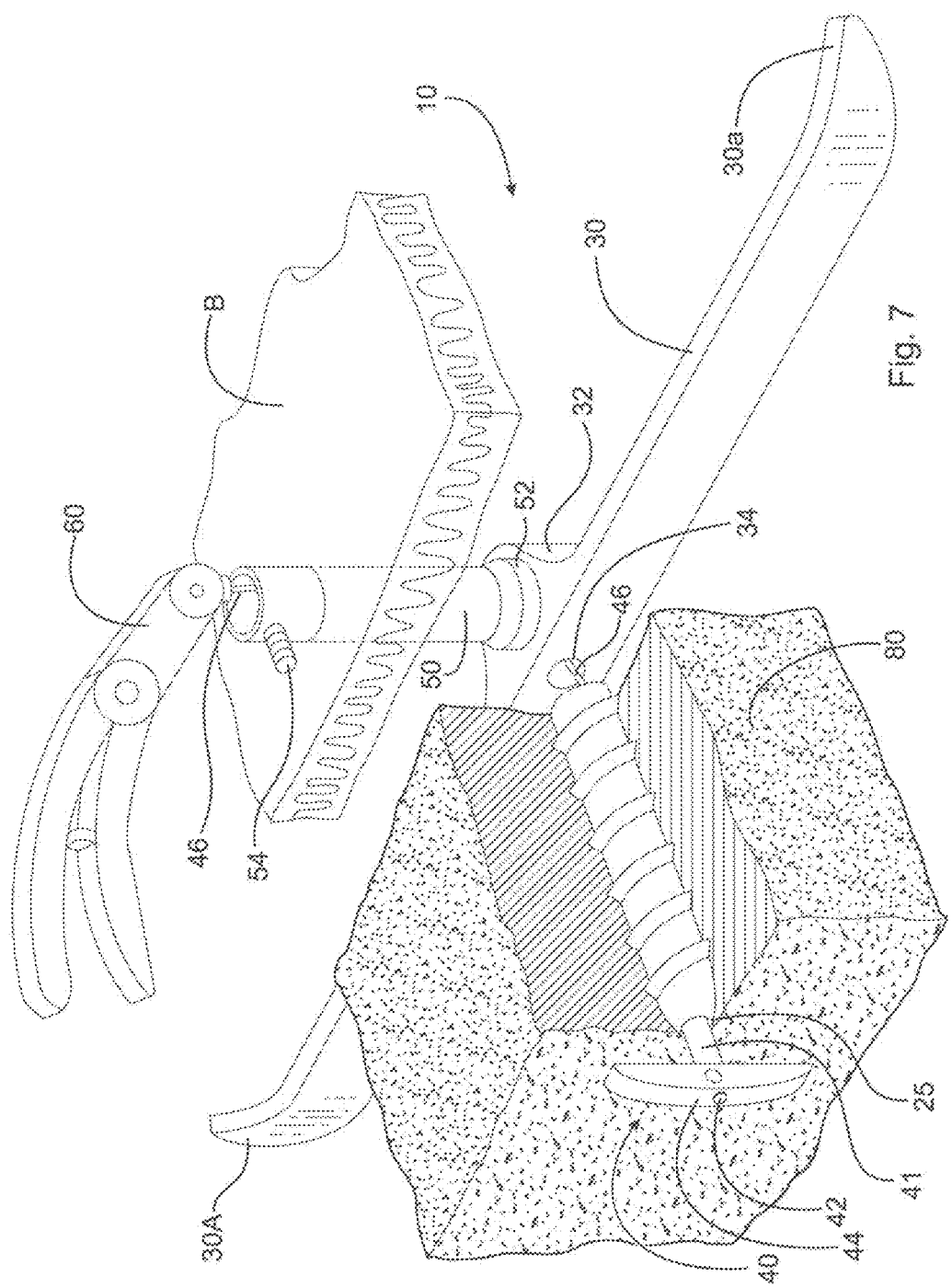
FIG. 7 is a side perspective partial exploded and fragmentary view of the assembly showing a pulling tool attached to the end of the pulling cable.

FIG. 7 is a side perspective partial exploded and fragmentary view of assembly 10 showing pulling tool 60 attached to the end of cable 46. Cable 46 has sufficient length to extend from the proximal end of the toggle bolt shaft to outside back B to be attached to pulling tool 60. Examples of pulling tools are winch or reel-type devices, come-along, pliers, screw jacks, or other suitable devices that are able to repeatedly apply a pulling force to cable 46 which pulls the convex apex of laterally curved spinal column 1 at the point where toggle wing 42 contacts vertebral body 80. Tube 50 is threadably attached to annular lip 38. It will be understood that other vertebra are positioned above and below target vertebra 80. Because rod 30 is placed along the concave curve of the spine, it is possible that it will not contact vertebra 80 during some or all of the alignment process as is shown in FIG. 7. The perpendicular turn allows the force vectors on cable 46 to be directed out of back B so that the lungs and surrounding viscera can be avoided.

Figure 8:
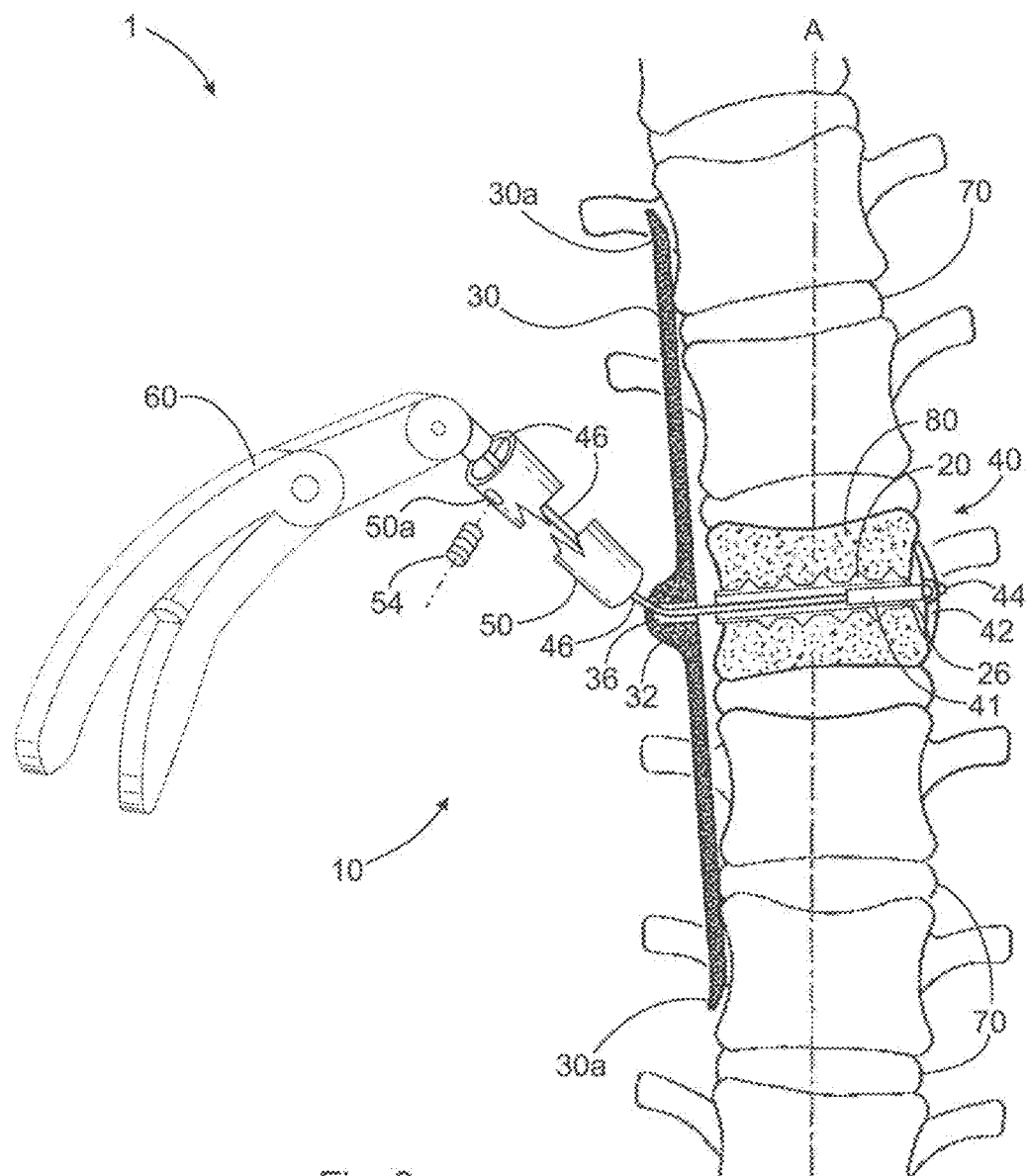
FIG. 8 is a top or posterior view of a laterally curved spinal column with the alignment assembly in place.

FIG. 8 is a top or posterior view of laterally curved spinal column 1 with alignment assembly 10 in place. Axis A represents what the longitudinal axis of spinal column 1 would be when straightened to the ideal anatomical position. Toggle bolt 40 is depicted with deployed wings 42 contacting vertebra 80. Vertebral discs 70 are shown alternately placed within spinal column 1 between each vertebra. The attachment of tube 50 to annular lip 38 is depicted in cut out form to show cable 46 extending from toggle bolt 40 through lumen 26 and aperture 36 into tube 50. In a preferred practice, tube 50 would be attached to annular lip 38. The further or distal end of cable 46 is attached to pulling tool 60. Rod 30 is placed laterally and longitudinally along spinal column 1. It can be seen that because rod 30 is preferably on the concave side of the lateral spinal curve, it may not contact curved spinal column 1 where cable 46 emerges from spinal column 1 on the concave or proximal side.

Figure 9:
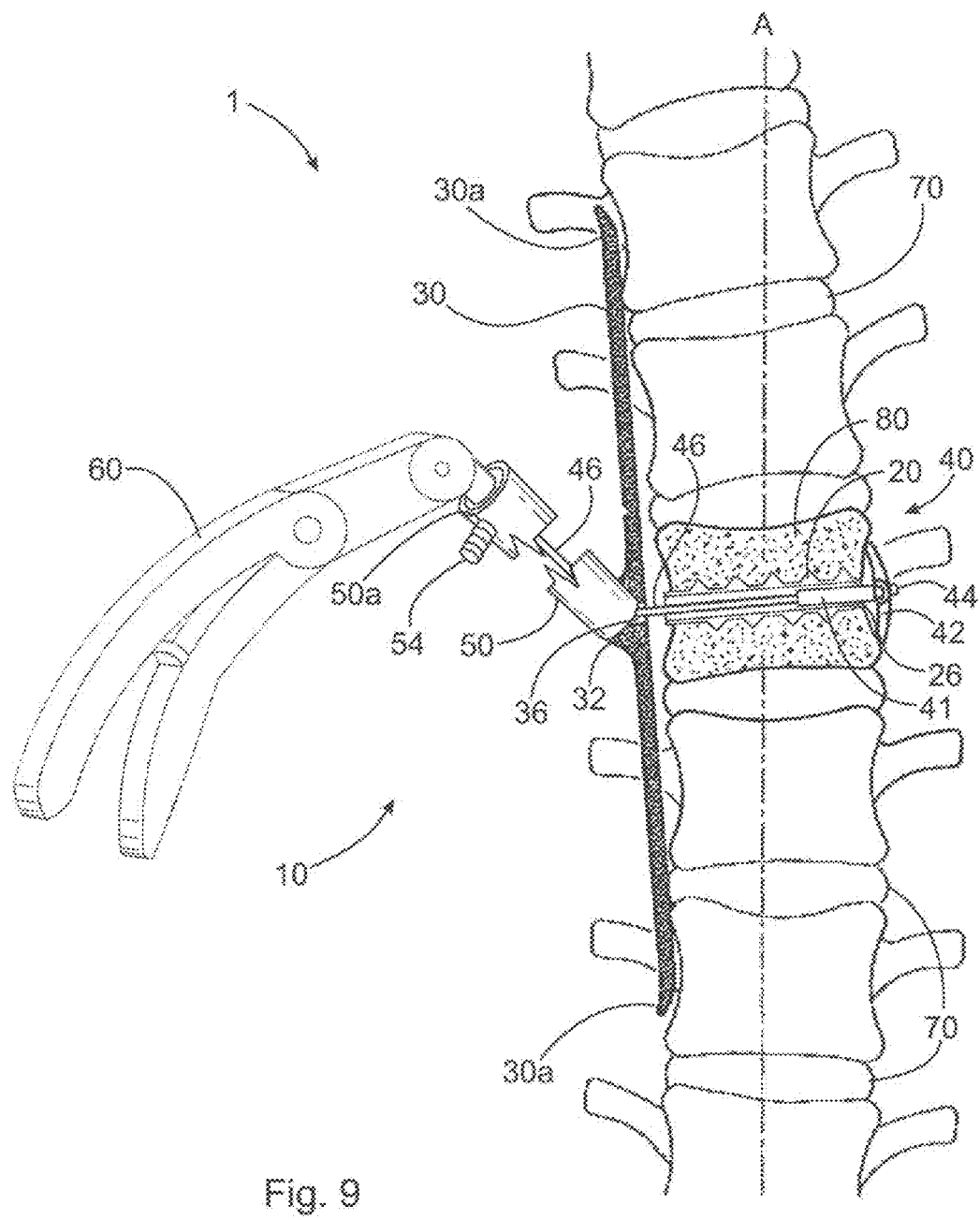
FIG. 9 is a top or posterior view showing the assembly holding the spinal column in place after a pulling procedure.

During the pulling procedure, set screw 54 is loosened or removed from tube aperture 50a. Pulling tool 60 applies pulling force across spinal column 1 onto wings 42. This pulls spinal column 1 against stabilizing rod 30 forcing wings 42 and consequently vertebra 80 toward rod 30 thereby reducing the lateral curve. After sufficient movement, tube set screw 54 is threaded into tube aperture 50a to hold the pulled cable and spinal column in the new straighter position. After a period of time to allow muscles and nerves and spinal column 1 to adjust to the new position, the pulling procedure is repeated with spinal column 1 again being pulled against rod 30 to an even straighter position relative to axis A. FIG. 9 shows assembly 10 after a pulling procedure with tube 50 attached to rod 30 at annular lip 38 (not shown in FIG. 9). By following the sequence of pulling, tightening, and waiting, spinal column 1 is gradually brought closer to proper alignment. In an example embodiment, alignment may be achieved of a period of as little as one or two days to as long as months, although in mild cases of scoliosis 5-15 minutes to one day may be possible. Normally, an alignment period may range from a week to about three months, but persons of skill in the art will recognize that the length of the alignment period will depend on such factors as the severity of the lateral curve, the age of the patient, and the strength of the surrounding neuromuscular structure as well as other factors.

Figure 10:
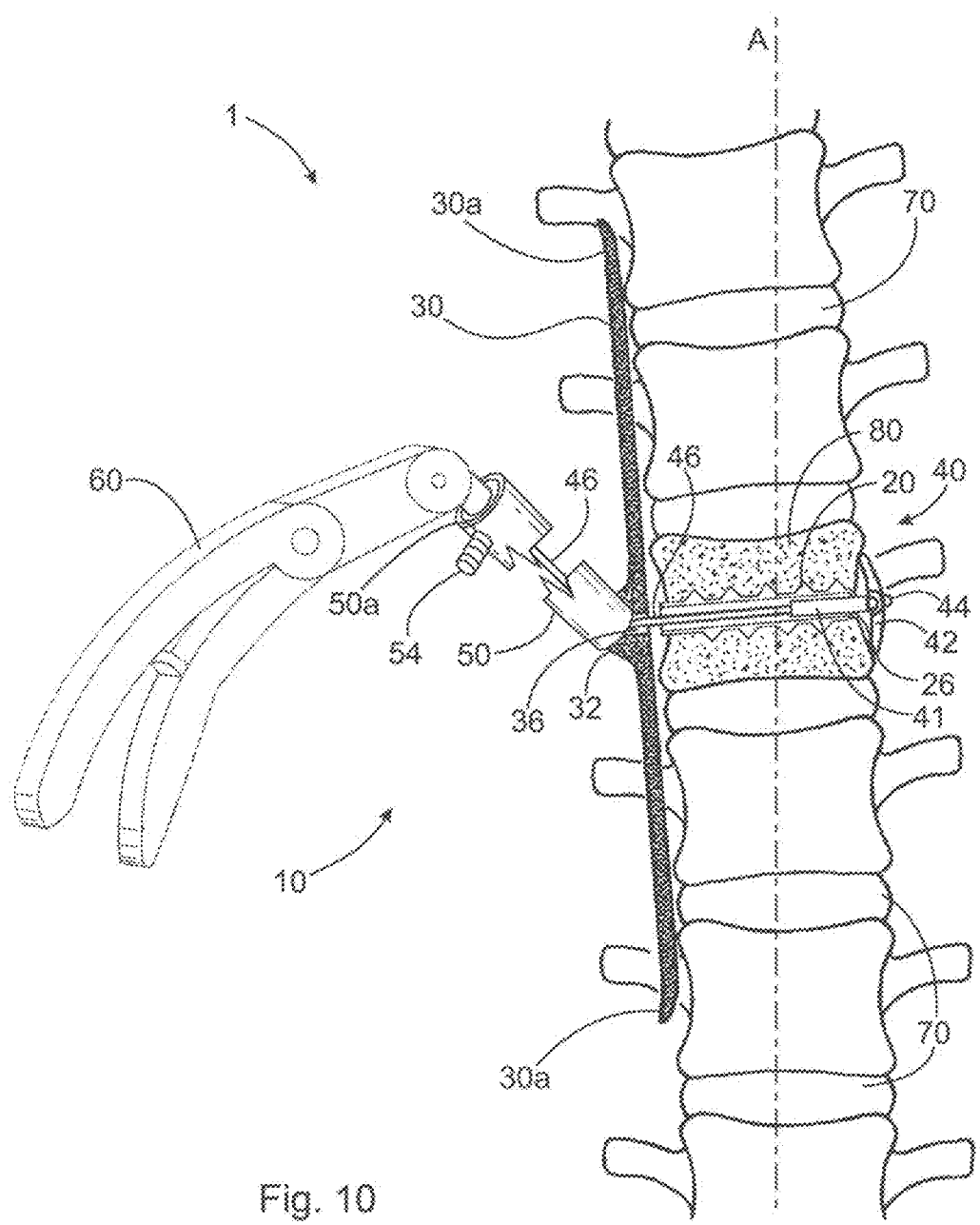
FIG. 10 shows the spinal column moved to a straighter position relative to the axis after a succeeding pulling procedure.
Figure 10A:
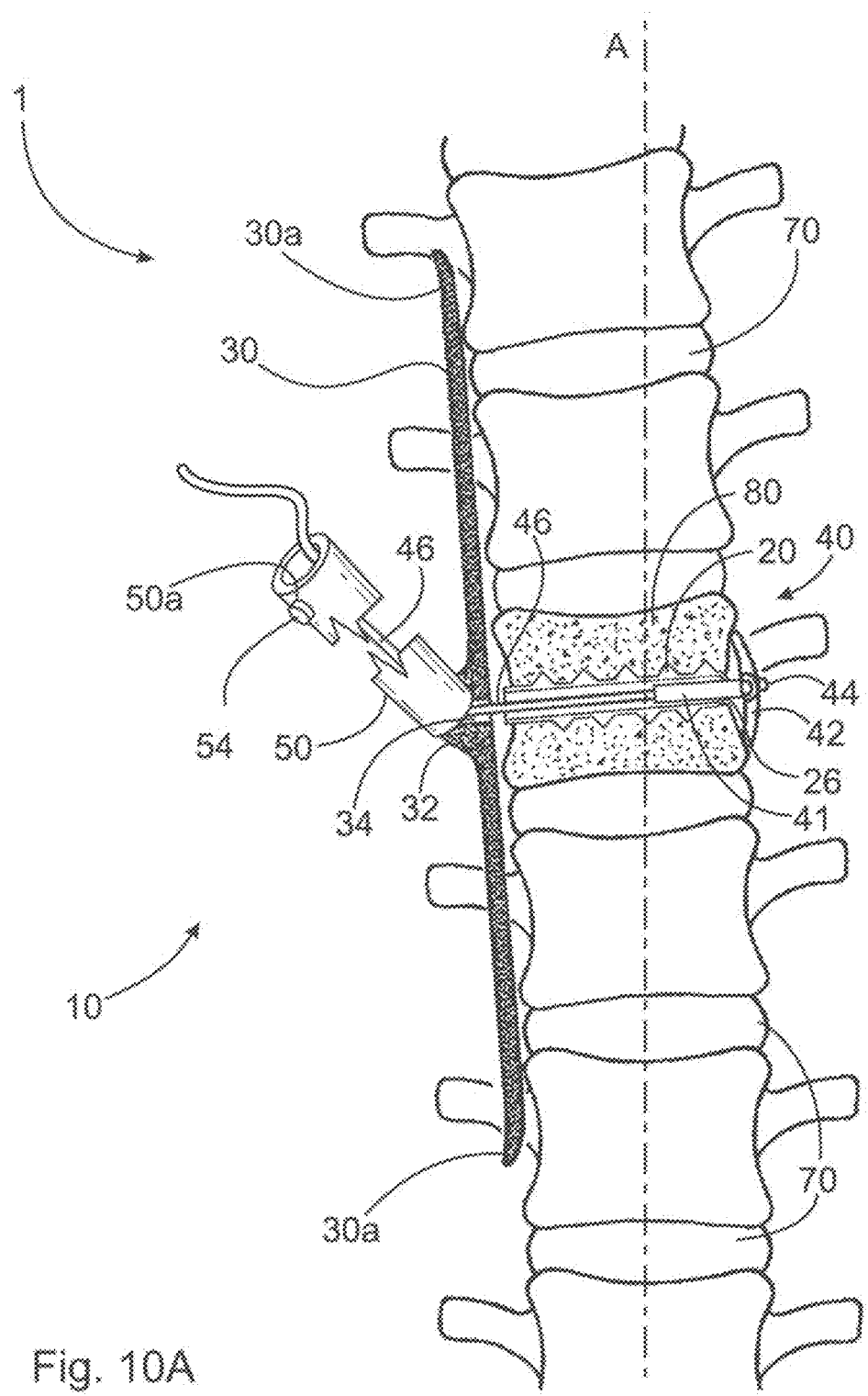
FIG. 10A shows the spinal column in FIG. 10 with the pulling tool removed and the tube set screw screwed into the tube aperture to hold the cable in place between pulling procedures.

FIG. 10 shows spinal column 1 moved to a straighter position relative to axis A after a succeeding pulling procedure. Rod 30 is shown closer to spinal column 1 as spinal column 1 is pulled straighter. It can also be seen that curved ends 30a provide an advantage over straight ends in that it allows stabilizing rod 30 to move along spinal column 1 with less if any interference with elements of spinal column 1. FIG. 10A shows assembly 10 with pulling tool removed and tube set screw 54 screwed into tube aperture 50a holding cable 46 in place between pulling procedures.

Figure 11:
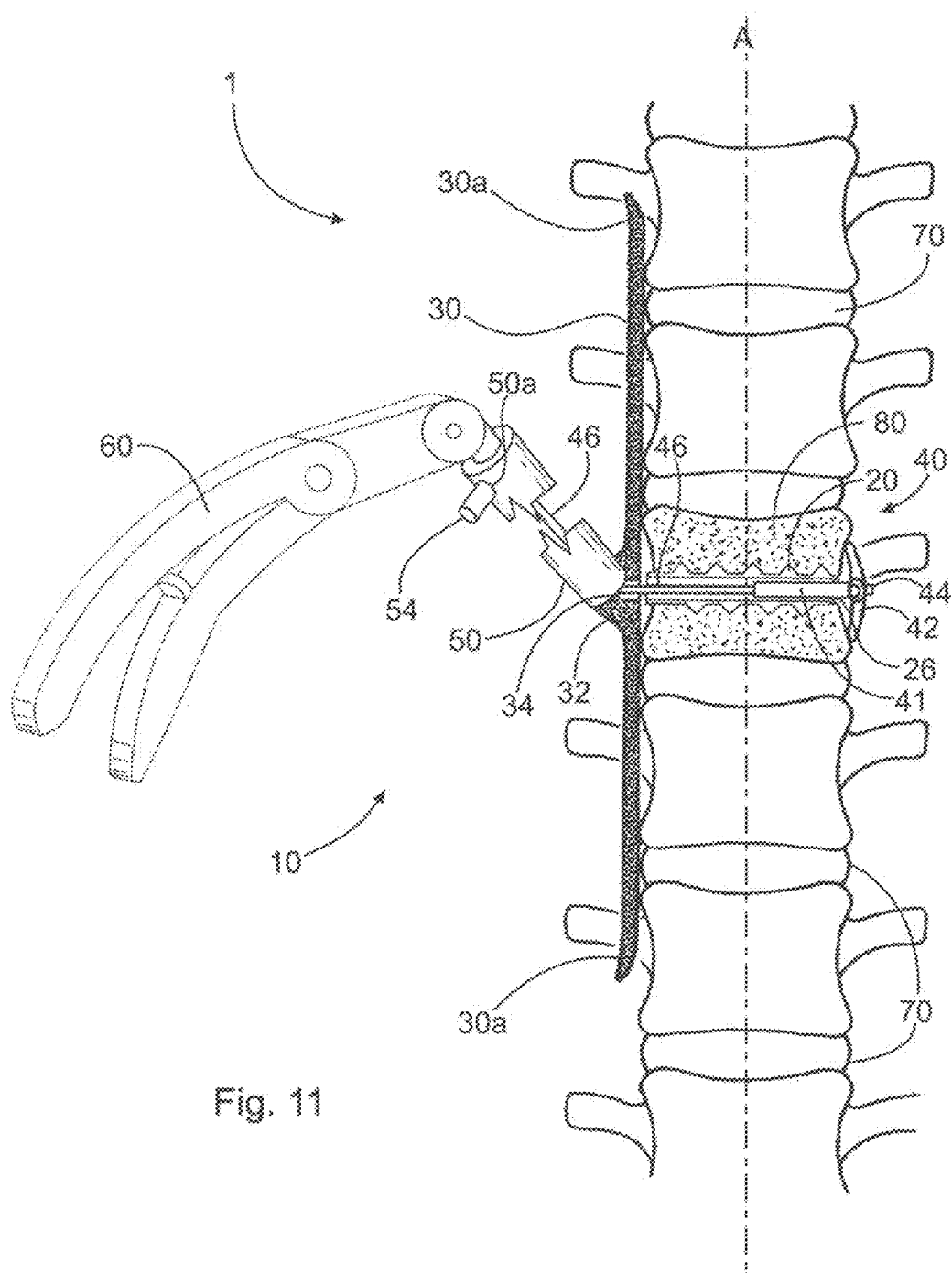
FIG. 11 is a top or posterior view of the spinal column shown in FIGS. 10 and 10A showing the results of the final pulling procedure in which the lateral curves of the spinal column is significantly reduced if not eliminated.

FIG. 11 is a top or posterior view of spinal column 1 showing the results of the final pulling procedure in which the lateral curve of spinal column 1 is significantly reduced if not eliminated. It can be seen that the middle section of stabilizing rod 30 is pulled close to vertebra 80 at the insertion point of hollow bone screw 20.

Figures 12, 12A:
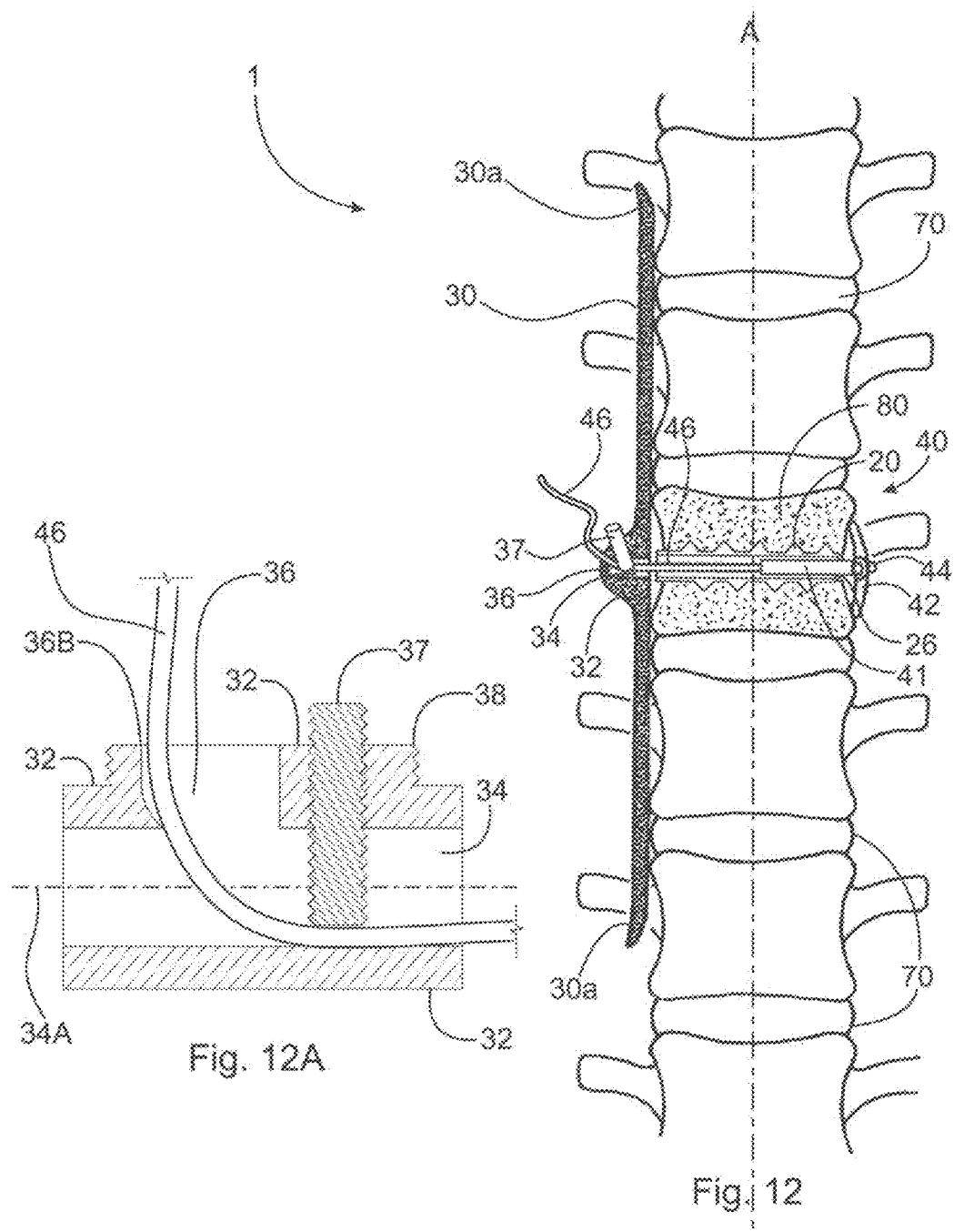
FIG. 12 is a posterior view showing spinal column after the final pulling procedure.
FIG. 12A is a cross sectional view similar to FIG. 5C showing the set screw holding the cable in place to maintain tension of the assembly after the final pulling procedure.

FIG. 12 is a posterior view showing spinal column 1 after the final pulling procedure. Tube 50 is removed through the back of the patient. Stabilizing rod 30 is left in place holding spinal column 1 in place against toggle bolt wings 42 with the holding force transmitted on cable 46 in lumen 26.

FIG. 12A is a cross section view similar to FIG. 5C in which set screw 37 is shown screwed down into screw hole 34 to hold (fix) cable 46 in place under tension after the final pulling procedure. Set screw 37 is screwed in place before set screw 54 is loosened to constantly maintain tension in cable 46 to enable assembly 10 to hold spinal column 1 in the final position. Set screw 37 may be tightened using appropriate conventional or arthroscopic instruments known to those skilled in the art. Thus, cable 46 is held in place under tension by its attachment to toggle bolt 40 at the distal end and by set screw 37 at the proximal end. After set screw 37 holds cable 46, the remaining "tail" of cable 46 extending past set screw 37 can be cut close to or inside aperture 38. In one embodiment, a cap may be placed over annular lip 38.

In an alternate embodiment, a percutaneous method of spinal alignment requiring no incisions employs puncture wounds to facilitate the placement of deployable bone anchors into or across chosen spinal elements such that tensile forces can be applied to specific areas of the spine thereby facilitating spinal alignment.

To achieve these ends, a standard Jamshidi needle, with removable central stylet, is passed across a chosen spinal element, such as a vertebra, from a direct lateral or a posterolateral approach depending on the desirability of avoiding intervening muscles or other structures.

Figure 13:
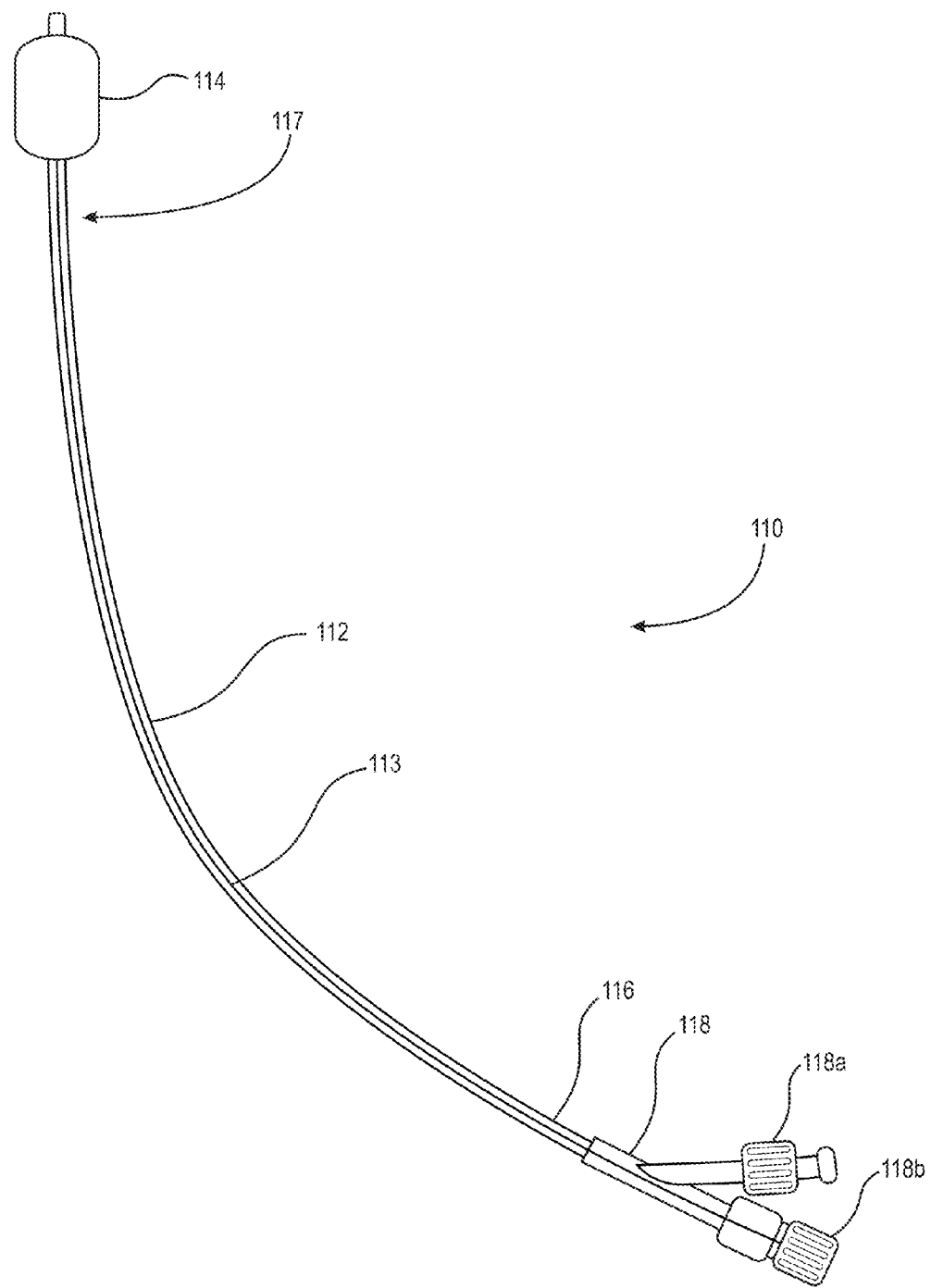
FIG. 13 is a top view of the inflatable balloon bone anchor which is a component of a second assembly utilized in the gradual alignment of a spine with one or more lateral curves.

FIG. 13 is a top view of inflatable balloon bone anchor 110 ("anchor 110") which is a component of assembly 100 utilized in the gradual alignment of a spine with one or more lateral curves. Anchor 110 includes hollow tube 112 with inflatable balloon 114 attached at distal end 117 with fluid conduit 118 ("conduit 118") attached to proximal end 116. Optionally, ports 118a and 118b extend from conduit 118 and receive the fluid(s) that may be used to inflate balloon 114 as explained below. Fluids may be introduced into tube 112 and balloon 114 through conduit 118. Preferably, tube 112 and balloon 114 are fabricated from polyglycolic acid or other similar biologically compatible absorbable material which can withstand the tensile or pulling strain created on anchor 110 as describe below and will also resorb into the body well after the alignment procedure is completed.

Figure 14A:
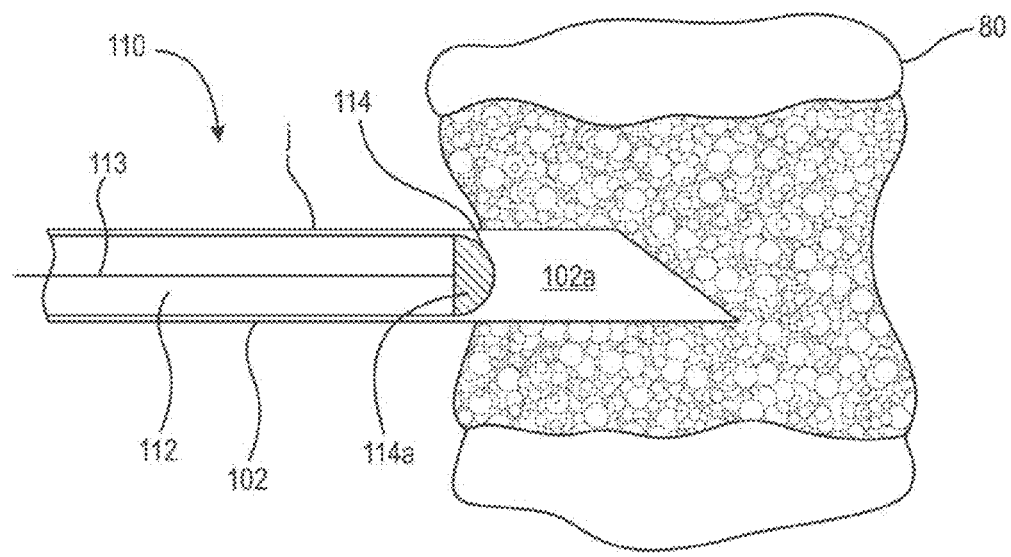
FIG. 14A is a cross sectional view of a target vertebra in which a Jamshidi needle is used to drill a hole into the target vertebra.
Figure 14B:
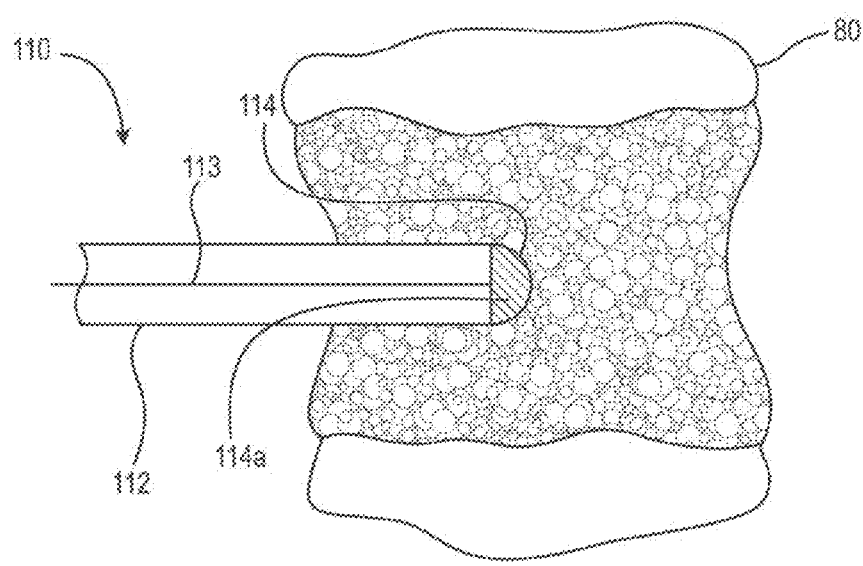
FIG. 14B is the same view as FIG. 14A depicting the Jamshidi needle withdrawn from around the balloon and tube.
Figure 14C:
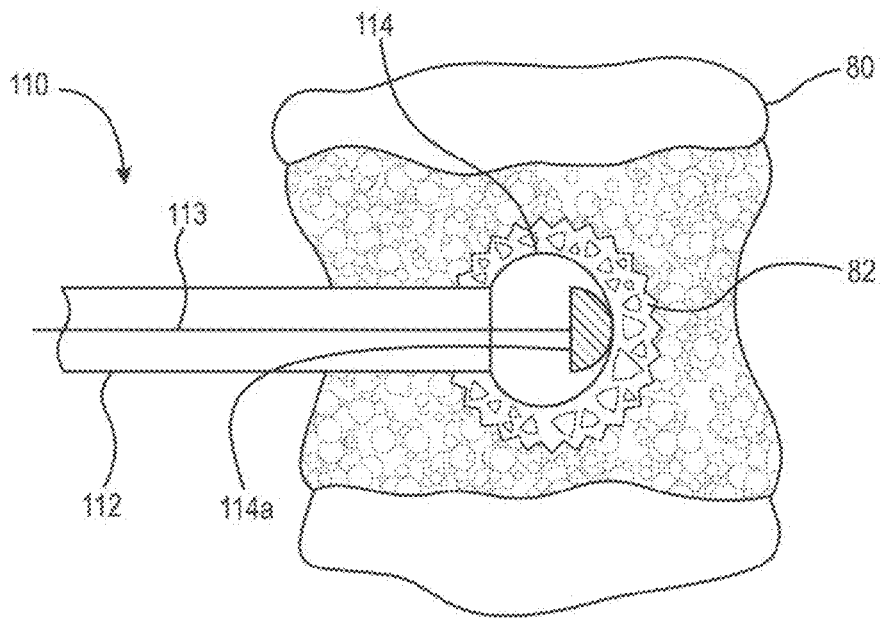
FIG. 14C shows the initiation of the inflation of the inflatable balloon inside the cancellous material at the core of the target vertebra.

FIG. 14A is a cross section view of target vertebra 80 in which a Jamshidi needle 102 ("needle 102") equipped with removable stylet 102a is used to drill a hole into vertebra 80. Inside needle 102 is the distal end 117 of tube 112 with uninflated balloon 114 contacting anchor tip 114a. Cable 113 is seen extending through tube 112 and attached to anchor tip 114a. FIG. 14B is the same view as FIG. 14A with stylet 102a removed from needle 102 and needle 102 withdrawn over tube 112 and from around balloon 114 and tube 112. In one embodiment, needle 102 is withdrawn before conduit 118 is attached to proximal end 116. FIG. 14C shows the initiation of the inflation of balloon 114 inside the cancellous material that forms the core of vertebra 80 while FIG. 14D depicts the withdrawal of anchor tip 114a resulting in the inflated balloon 114 creating and lining a cavity 82 to become embedded within the cancellous bone material.

Figure 14D:
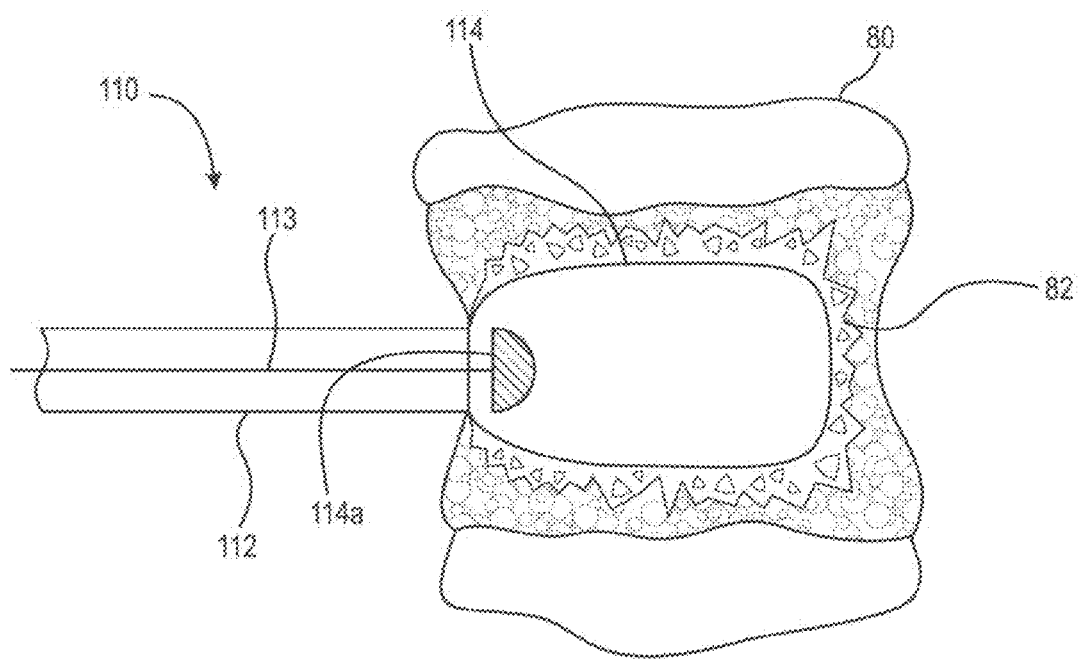
FIG. 14D depicts the withdrawal of the anchor tip resulting in the inflated balloon lining a cavity created within the cancellous bone material.

FIGS. 14C and 14D depict the inflation of balloon 114 through a hydraulic method in which fluid is introduced through ports 118a and/or 118b and passes into balloon 114 through tube 112. As fluid volume increases, balloon 114 increases in size to create cavity 82 in the cancellous material. For temporary anchor fixation, water or saline may be used to inflate balloon 114. Permanent fixation may be achieved with hardenable materials such as bone putty or methyl methylacrylate (MMA) as is known to those having skill in the art.

Figure 15A:
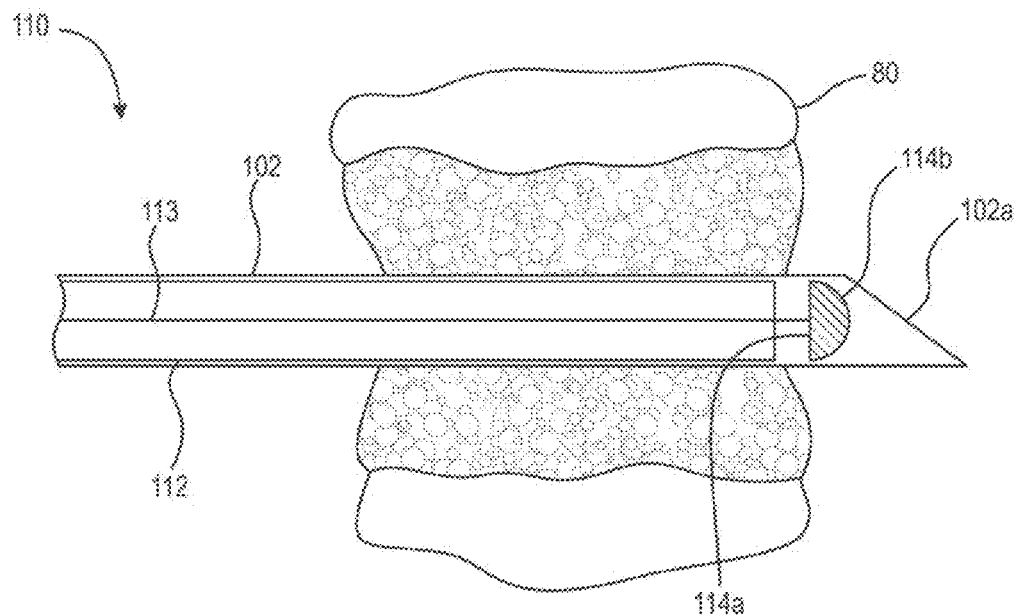
FIG. 15A depicts a second method of attaching the inflatable balloon anchor to a vertebra in which the Jamshidi needle is drilled through the vertebra to create a passage extending through the opposing sides of the vertebra.
Figure 15B:
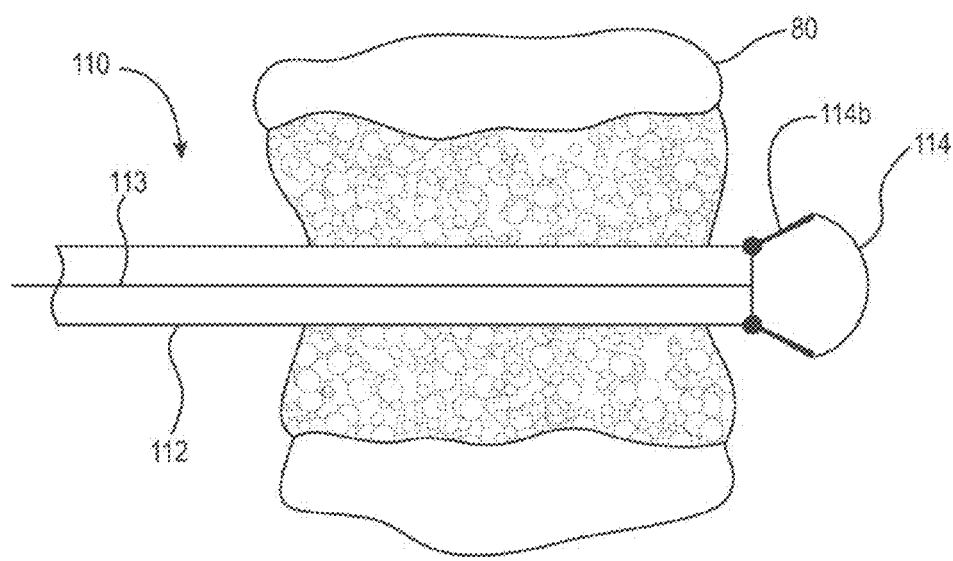
FIG. 15B shows the Jamshidi needle withdrawn from around the inflatable balloon catheter and the balloon starting to inflate.
Figure 15C:
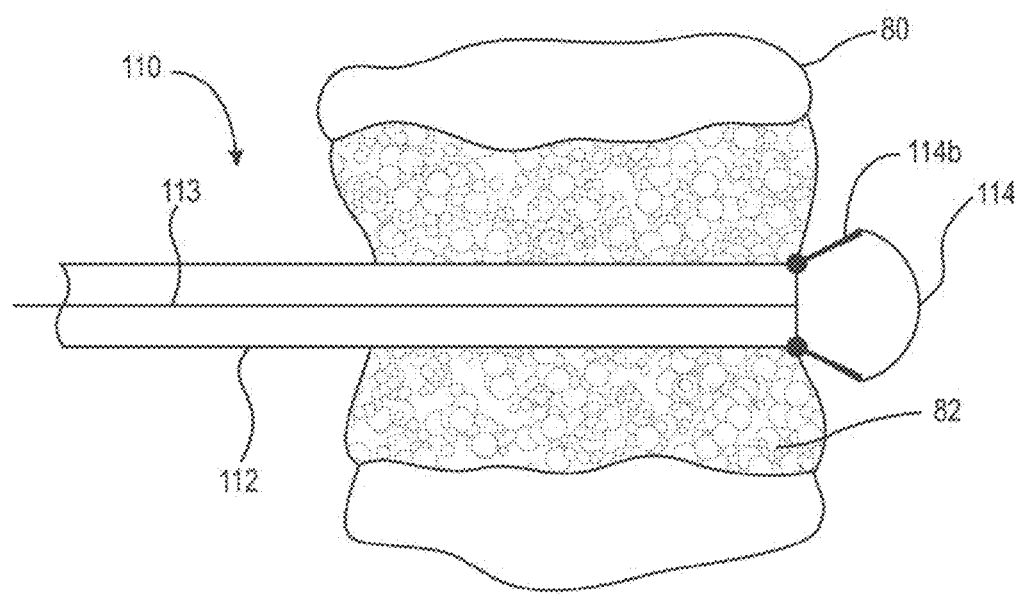
FIG. 15C shows the inflatable balloon drawn against the side of the target vertebra opposing the side where the balloon bone anchor enters the vertebra (proximal side)
Figure 15D:
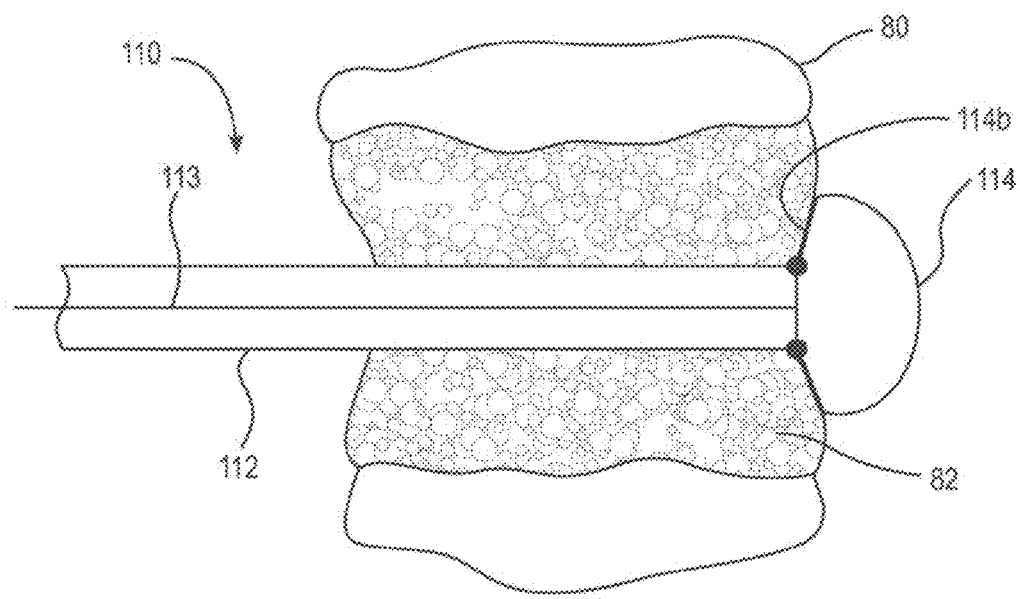
FIG. 15D depicts the fully inflated balloon drawn against the vertebra.

FIG. 15A depicts a second method of attaching anchor 110 to vertebra 80. Needle 102 is drilled through vertebra 80 to create a passage extending through opposing sides of vertebra 80. Similar to the method described above, it can be seen that anchor 110 is carried inside needle 102 during the drilling process. FIG. 15B shows stylet 102a removed and needle 102 withdrawn from around anchor 110 with balloon 114 starting to inflate. FIG. 15C shows balloon 114 drawn against the side of vertebra 80 (distal side) opposing the side where tube 112 enters vertebra 80 (proximal side). FIG. 15D depicts fully inflated balloon 114 drawn against vertebra 80.

FIGS. 15B-15D depict an alternate embodiment of an apparatus for mechanically deploying balloon 114. Array 114b comprises a plurality of arms or vanes operatively attached to the inner surface of balloon 114 and pivotally attached to cable 113. The term "operatively attached" means that a component or device is connected either directly or indirectly to a second component and causes that second component to function. For example, each of the plurality of arms in array 114b is operatively attached to the inner surface of balloon 114 and causes balloon 114 to open. When cable 113 is pulled, the arms of array 114b each open causing balloon 114 to inflate. Array 114b may be used to open balloon 114 when greater pulling or fraction forces are necessary during the aligning process as explained below. It will be recognized that the mechanical inflation method may be used to form cavity 82 and embed balloon 114 as seen in FIGS. 14C and 14D. Conversely, the hydraulic method described above may be used to inflate balloon 114 and draw it toward vertebra 80 as seen in FIGS. 15C and 15D.

Figure 16:
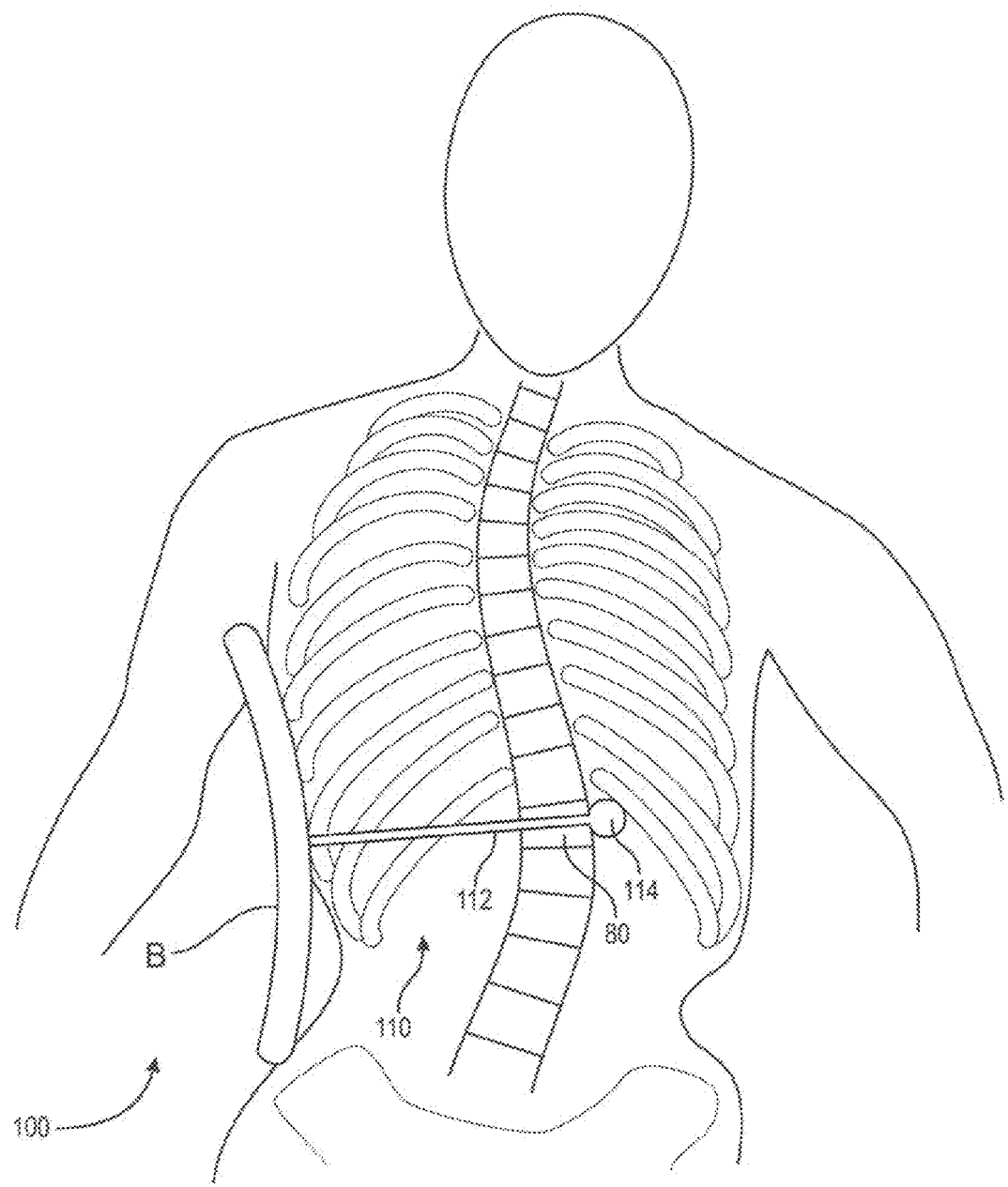
FIG. 16 is a schematic front view of the inflatable balloon catheter attached to an external leverage support to form the second embodiment of the present invention.

FIG. 16 is a schematic front view of anchor 110 attached to an external leverage support B to form assembly 100. In the front view shown, tube 112 extends through vertebra 80 with inflatable balloon 114 drawn against side of vertebra 80 on the convex side of the lateral curve of the spinal column. After balloon 114 is inflated, tube 112 is releasably attached to external leverage support B, in this case external body brace ("brace B") similar to that seen in FIG. 1 and otherwise described above. Proximal end 116 is attached to brace B. To effect the attachment outside the body, a small incision may be made to pass tube 112 through the skin and releasably attach it to brace B. Attachment may be made similar to that seen above with assembly 10 in which cable 46 is pulled and tied against stabilizing bar 30. Pulling tools such as come alongs, winches, pliers, etc. attached to proximal end 116 may be used.

Because the attachment to vertebra 80 is percutaneous and reversible, multiple points of attachment can be selected to resolve multiple curve issues as well as to spread corrective force over more than target vertebra 80 so that excessive force on a single cable is not required. Partial external braces B may be used opposite each series assemblies 100 to direct the required pulling force more precisely. This provides the advantage of obviating the need for the large external braces presently in use. In a preferred embodiment, the braces may have movable pads or points of contact to prevent applying the pulling force at the same site on the skin.

Figure 17:
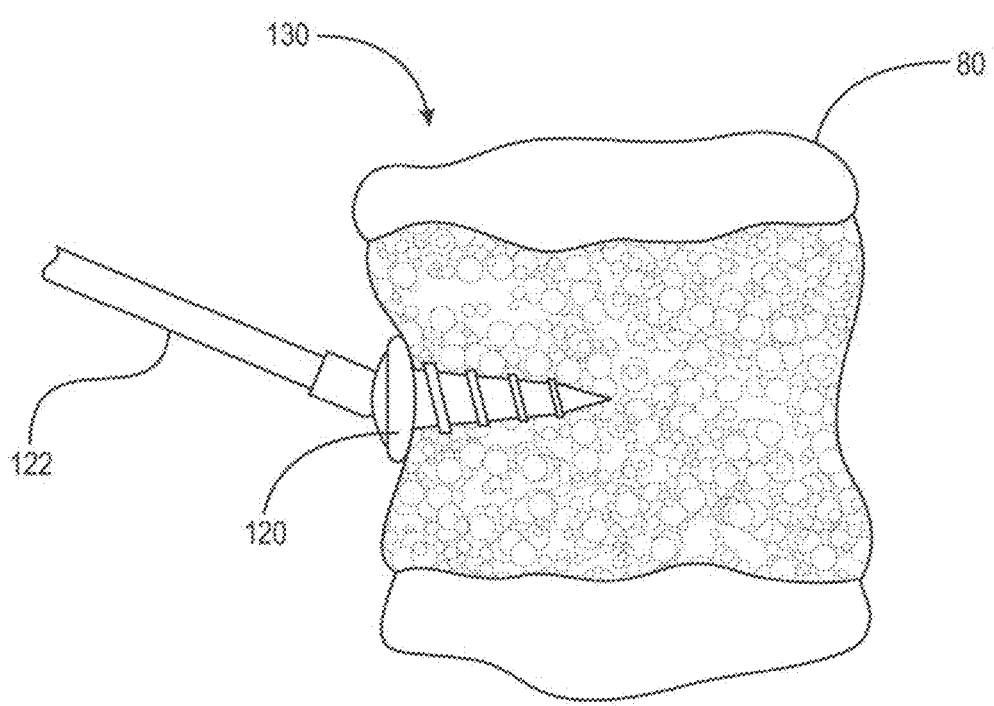
FIG. 17 is a cross sectional view of a bone screw embedded into vertebra and attached to a strut.

FIG. 17 is a cross sectional view of bone screw 120 embedded into vertebra 80 and attached to strut 122. This bone screw-strut construction 130 ("construction 130") can be used to apply pushing force on the lateral curve by turning strut 122, which is attached to brace B', toward embedded bone screw 120, thereby pushing the lateral curve into alignment. Preferably, bone screw 120 is attached to strut 122 by a hinge or other polyaxial connection to allow different vector angles of force to be applied to bone screw 120 as is pushes on the lateral curve.

Figure 18A:
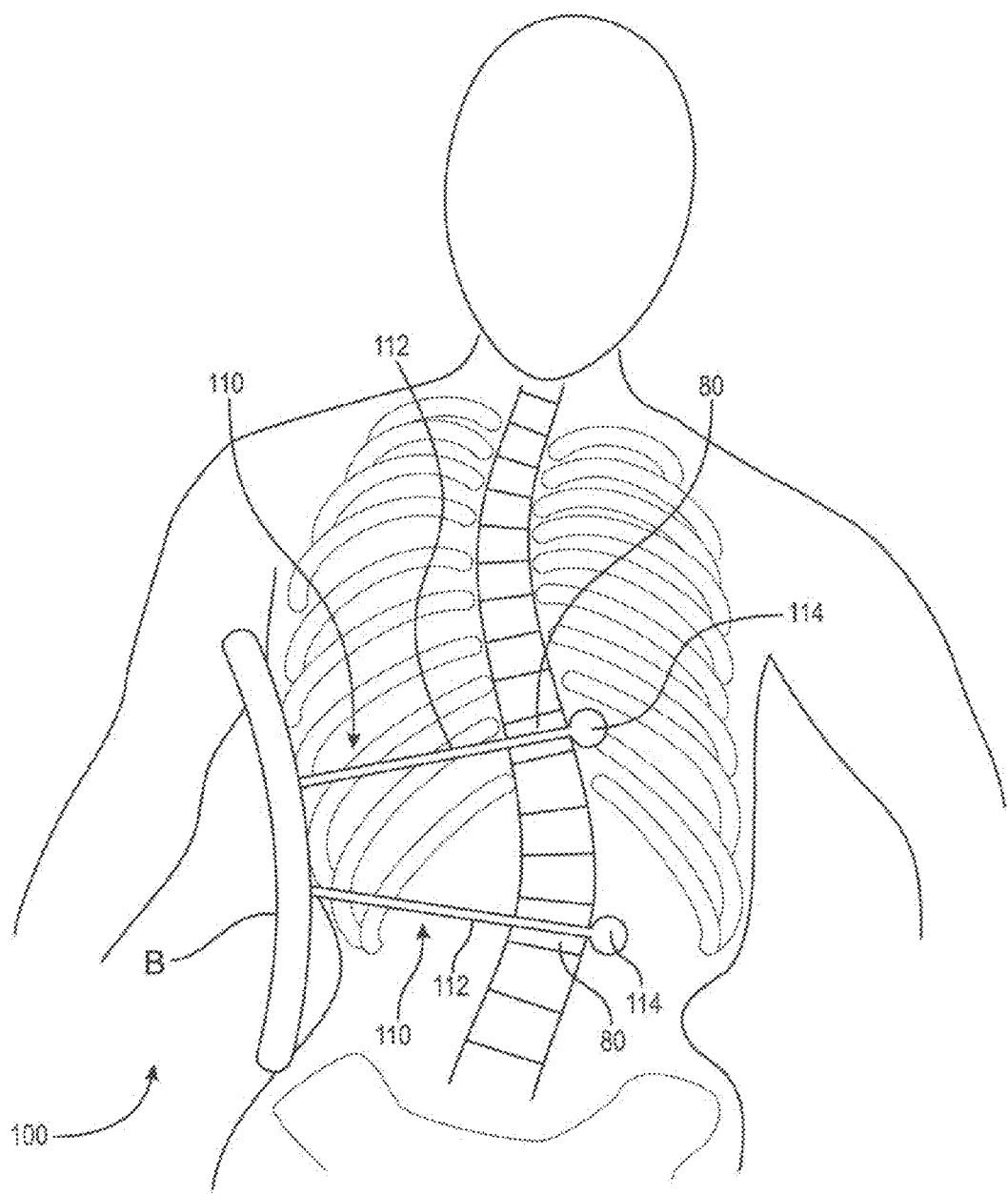
FIG. 18A is a schematic view of the use of two balloon anchor assemblies to pull the spinal column into alignment; and, FIG. 18B depicts schematically the use of the bone screw construction with one or more balloon anchor assemblies to combine both pulling and pushing forces to simultaneously apply corrective pressure on both sides of the lateral curve.

FIG. 18A is a schematic view of the use of two assemblies 100 to pull the spinal column into alignment. It can be seen that anchors 110 are attached to vertebrae 80 with balloons 114 contacting vertebrae 80 on the convex side of the lateral curve. This arrangement provides the advantage of reducing the forces applied to the components bone anchor 110 as well as to the spinal column itself.

Figure 18B:
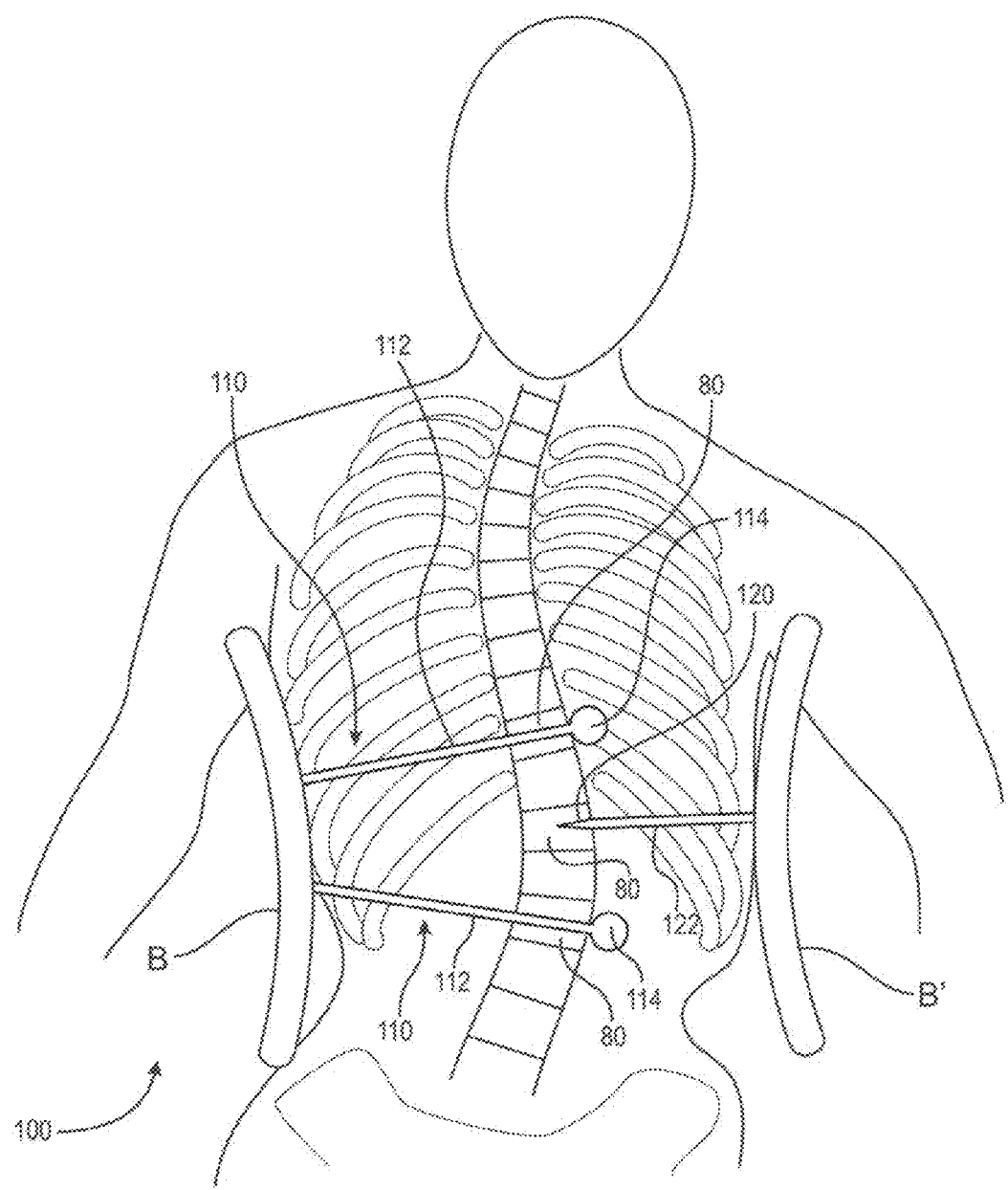

FIG. 18B depicts schematically the use of bone screw construction 130 with one or more assemblies 100 to combine both pulling and pushing forces to apply corrective forces on both sides of the lateral curve. Construction 130 is attached to brace B' on the opposite side of spine from assembly 100. It will be recognized that brace B' may be the same or a different external support than support B attached to assembly 100. Bone screw 120 may be used to push the lateral curve into alignment by screwing strut 122, threadably attached to brace B', toward the convex side of the lateral curve thereby pushing it into alignment. FIG. 18B also shows two assemblies 100 pulling two portions of the same lateral curve into alignment demonstrating the attachment of assembly 100 to multiple points on the spine.

Assembly(ies) 100 are used in a manner similar to that used for assembly 10 described above. With anchor 110 attached to target vertebra 80, and proximal end 116 attached to brace B, tube 112 is pulled toward brace B to pull the lateral curve closer to alignment. After the pulling process, tube 112 is attached to brace B in such a way as to hold catheter 110 in the pulled position, thereby holding the lateral curve in its new position closer to the desired alignment. The pulling process and the results of the pulling process can be observed with MRI, x-rays, etc. to determine how much to pull catheter 110 each time. By repeating the "pull-tie off" process, the lateral curve can gradually be brought into or closer to alignment without disrupting surrounding tissue and nerves. Similarly, bone construction 130 may supplement assembly(ies) 100 to gradually push the spine into the desired alignment Once the desired spinal alignment had been achieved over a period of time, much like braces are used to align teeth, the spine can be fused using endoscopic techniques and the deployed anchors can be contracted and removed or dissolve into the body. Alternatively, percutaneous alignment could be maintained until skeletal maturity is reached, potentially obviating the need for surgery entirely.

Thus it is seen that the objects of the invention are efficiently obtained, although changes and modifications to the invention should be readily apparent to those having ordinary skill in the art, which changes would not depart from the spirit and scope of the invention as claimed.

I claim:

1. A percutaneous implantable device for aligning a spine having a plurality of vertebra, comprising:
   a tube having a proximal end and a distal end, the tube arranged to extend through a hole in a vertebra of the spine;
   a cable extending within the tube, the cable secured to the distal end of the tube;
   an anchor tip attached to the cable;
   an inflatable balloon secured to the distal end of the tube and arranged to inflate against an external surface of the vertebra and completely enclose the anchor tip; and,
   a leverage support releasably attached to the proximal end of the tube, wherein when the inflatable balloon is inflated, the cable and inflated balloon are arranged for pulling the vertebra towards the leverage support.

2. The percutaneous implantable device recited in claim 1, further comprising a pulling device attached to the proximal end of the tube.

3. The percutaneous implantable device recited in claim 2, wherein the pulling device is pliers.

4. The percutaneous implantable device recited in claim 2, wherein the pulling device is a winch.

5. The percutaneous implantable device recited in claim 2, wherein the pulling device is a screw jack.

6. The percutaneous implantable device recited in claim 2, wherein the pulling device is a come-along.

7. The percutaneous implantable device recited in claim 1, wherein the tube is fabricated from polyglycolic acid.

8. The percutaneous implantable device recited in claim 1, wherein the inflatable balloon is inflated hydraulically.

9. The percutaneous implantable device recited in claim 1, wherein the inflatable balloon is inflated mechanically.

10. A percutaneous implantable device for aligning a spine having a plurality of vertebra, comprising:
    a tube having a proximal end and a distal end, the tube arranged to extend into an opening in a vertebra of the spine;
    a cable extending within the tube, the cable secured to the distal end of the tube;
    an anchor tip attached to the cable;
    an inflatable balloon secured to the distal end of the tube and arranged to inflate within the opening in the vertebra and completely enclose the anchor tip; and,
    a leverage support releasably attached to the proximal end of the tube, wherein when the inflatable balloon is inflated, the cable and inflated balloon are arranged for pulling the vertebra towards the leverage support.

* * * * *